US012357535B2

(12) United States Patent
Cleveland et al.

(10) Patent No.: US 12,357,535 B2
(45) Date of Patent: Jul. 15, 2025

(54) ARTICULATING BIOCONTAINERS

(71) Applicant: EMD Millipore Corporation, Burlington, MA (US)

(72) Inventors: Shannon Cleveland, Hudson, NH (US); Marina Varlamova, Malden, MA (US); John Saragosa, Melrose, MA (US); David DeCoste, Chelmsford, MA (US); Benjamin Cacace, Tewksbury, MA (US); Daniel Lamothe, Burlington, MA (US); George Gagne, Dracut, MA (US); James Dee, Burlington, MA (US); Wilson Moya, Carlise, MA (US); Stefano Berti Perez, Boston, MA (US)

(73) Assignee: EMD Millipore Corporation, Burlington, MA (US)

( * ) Notice: Subject to any disclaimer, the term of this patent is extended or adjusted under 35 U.S.C. 154(b) by 257 days.

(21) Appl. No.: 17/639,973

(22) PCT Filed: Sep. 9, 2020

(86) PCT No.: PCT/US2020/049846
§ 371 (c)(1),
(2) Date: Mar. 3, 2022

(87) PCT Pub. No.: WO2021/050484
PCT Pub. Date: Mar. 18, 2021

(65) Prior Publication Data
US 2022/0323300 A1    Oct. 13, 2022

Related U.S. Application Data

(60) Provisional application No. 62/898,402, filed on Sep. 10, 2019.

(51) Int. Cl.
*A61J 1/10*        (2006.01)
*B32B 3/30*        (2006.01)
(Continued)

(52) U.S. Cl.
CPC .................. *A61J 1/10* (2013.01); *B32B 3/30* (2013.01); *B32B 5/022* (2013.01); *B32B 5/024* (2013.01);
(Continued)

(58) Field of Classification Search
CPC ......... A61J 1/10; B65D 21/086; B65D 25/54; B65D 88/18; B65D 2207/00; C12M 23/14; C12M 23/26; C12M 41/44; G01M 3/3218
(Continued)

(56) References Cited

U.S. PATENT DOCUMENTS 2,400,716 A * 5/1946 Sattler .................... B65D 35/10
                                                                426/115
4,526,296 A * 7/1985 Berger ................. B65D 1/0292
                                                                222/107
(Continued)

FOREIGN PATENT DOCUMENTS

AU    2007200996 A1    3/2007
CN       1261320 A     7/2000
(Continued)

OTHER PUBLICATIONS

Office Action received for Japanese Patent Application No. 2022-541191 mailing date Apr. 4, 2023, 13 Pages (7 Pages of English Translation and 6 Pages of Official Copy).
(Continued)

*Primary Examiner* — Jes F Pascua
(74) *Attorney, Agent, or Firm* — EMD Millipore Corporation

(57) ABSTRACT

A biocontainer having a first film, the film having an interior and exterior side; articulating elements disposed on or within the first film, the articulating elements comprising at least one a folded hinge, a sealed joint, a thinned pathway, a bowed path, an embedded polymeric or metallic cylindri-
(Continued)

cal fiber or rod; and a second film, optionally comprising articulating elements, joined to the first film, to form a biocontainer having a closed volume, wherein the articulating elements permit the biocontainer to expand and collapse along the articulating elements.

15 Claims, 17 Drawing Sheets

(51) Int. Cl.
    *B32B 5/02*     (2006.01)
    *B32B 27/12*     (2006.01)
    *B32B 27/32*     (2006.01)
    *B65D 21/08*     (2006.01)
    *B65D 25/54*     (2006.01)
    *B65D 88/18*     (2006.01)
    *C12M 1/00*     (2006.01)
    *C12M 1/34*     (2006.01)
    *G01M 3/32*     (2006.01)
    *B32B 27/30*     (2006.01)

(52) U.S. Cl.
    CPC .............. *B32B 27/12* (2013.01); *B32B 27/32* (2013.01); *B65D 21/086* (2013.01); *B65D 25/54* (2013.01); *B65D 88/18* (2013.01); *C12M 23/14* (2013.01); *C12M 23/26* (2013.01); *C12M 41/44* (2013.01); *G01M 3/3218* (2013.01); *B32B 27/306* (2013.01); *B32B 2307/726* (2013.01); *B65D 2207/00* (2013.01)

(58) Field of Classification Search
    USPC .................................................. 383/109, 105
    See application file for complete search history.

(56) References Cited

U.S. PATENT DOCUMENTS

| | | | |
|---|---|---|---|
| 5,988,422 A | 11/1999 | Vallot | |
| 9,637,716 B2 | 5/2017 | Dahlberg et al. | |
| 2002/0009575 A1 | 1/2002 | DeMatteis | |
| 2007/0272705 A1* | 11/2007 | Beine | B32B 27/32 |
| | | | 222/105 |
| 2014/0193897 A1 | 7/2014 | Dahlberg et al. | |
| 2017/0368790 A1 | 12/2017 | Decoste et al. | |
| 2018/0142200 A1 | 5/2018 | Mason et al. | |
| 2019/0256270 A1* | 8/2019 | Bazin | A61J 1/10 |

FOREIGN PATENT DOCUMENTS

| | | | | |
|---|---|---|---|---|
| CN | 101180216 A | 5/2008 | | |
| DE | 537401 C | 11/1931 | | |
| EP | 1012227 A1 | 6/2000 | | |
| EP | 2898055 A1 | 7/2015 | | |
| EP | 3274168 A1 | 1/2018 | | |
| GB | 2189773 A | * 11/1987 | ........... | B65D 19/385 |
| JP | S57-188690 A | 11/1982 | | |
| JP | S57-188690 U | 11/1982 | | |
| JP | S63-108733 A | 5/1988 | | |
| JP | 2533194 Y2 | 4/1997 | | |
| JP | 2007-050556 A | 3/2007 | | |
| JP | 2008-105752 A | 5/2008 | | |
| JP | 2008-212049 A | 9/2008 | | |
| JP | 2009-136687 A | 6/2009 | | |
| JP | 2009-227341 A | 10/2009 | | |
| JP | 2010-030264 A | 2/2010 | | |
| JP | 2013-074889 A | 4/2013 | | |
| JP | 2018-515144 A | 6/2018 | | |
| JP | 2018-516209 A | 6/2018 | | |
| JP | 2018-161145 A | 10/2018 | | |
| JP | 2020054392 A | * 4/2020 | | |
| KR | 10-2018-0011216 A | 1/2018 | | |
| WO | 2008/089510 A1 | 7/2008 | | |
| WO | 2014/121918 A1 | 8/2014 | | |
| WO | WO-2014191947 A1 | * 12/2014 | ........... | C12M 21/14 |
| WO | 2016/154180 A1 | 9/2016 | | |
| WO | 2016/185221 A1 | 11/2016 | | |
| WO | 2018/087558 A1 | 5/2018 | | |
| WO | 2021/050484 A1 | 3/2021 | | |

OTHER PUBLICATIONS

International Search Report and Written Opinion for International Application No. PCT/US2020/049846, mailed on Feb. 1, 2021, 20 pages.
Office Action received for Japanese Patent Application No. 2022-541191 mailing date Sep. 26, 2023, 13 Pages (7 Pages of English Translation and 6 Pages of Official Copy).
Office Action received for Canadian Patent Application No. 3,153,689 mailing date Mar. 21, 2023, 3 Pages.
Office Action received for Korean Patent Application No. 10-2022-7011755 mailing date Mar. 15, 2024, 17 Pages (8 Pages of English Translation & 9 Pages of Official Copy).
Office Action received for Japanese Patent Application No. 2022-541191 mailing date Mar. 12, 2024, 11 Pages (5 Pages of English translation & 6 Pages of Official copy).
CINPA Office Action for Chinese Application No. 2020800636909, dated Apr. 11, 2025, 15 pages (8 pages of OA, 7 pages of English Translation).

* cited by examiner

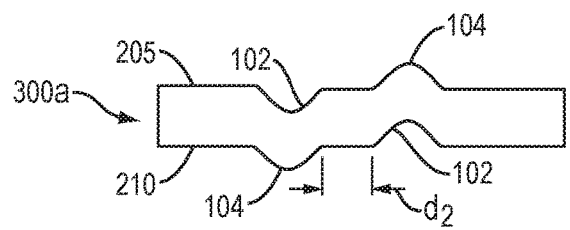
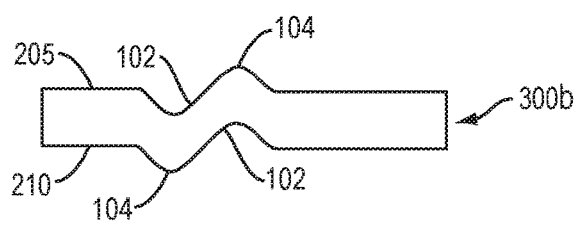
FIG. 3A  FIG. 3B
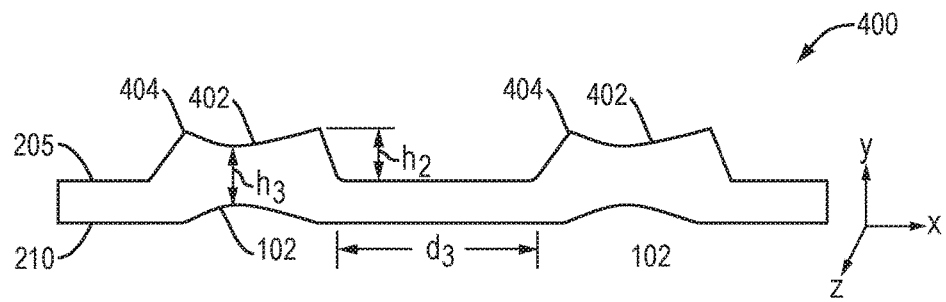
FIG. 4
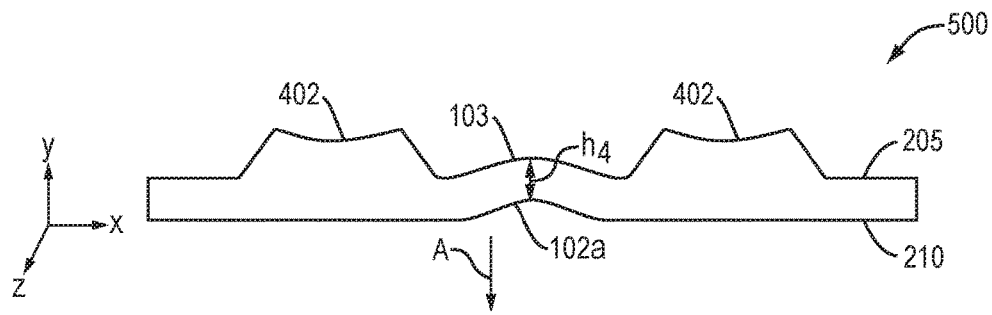
FIG. 5

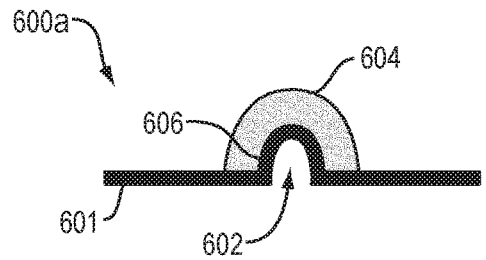
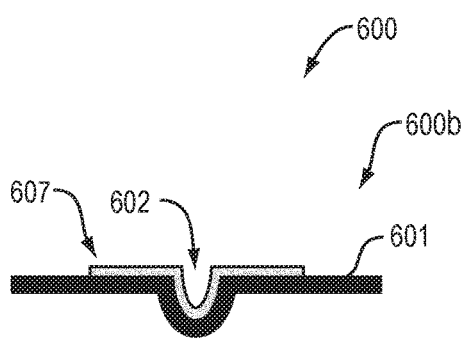
FIG. 6A                FIG. 6B
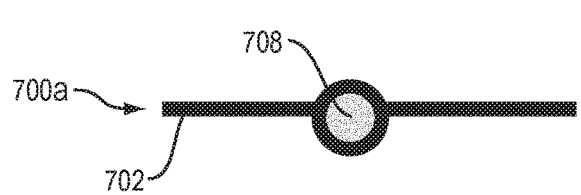
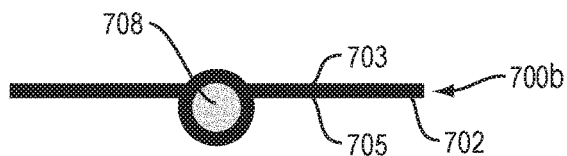
FIG. 7A                FIG. 7B
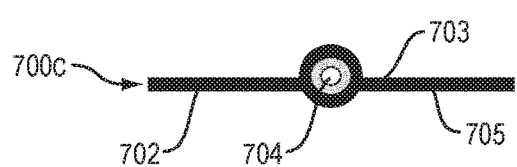
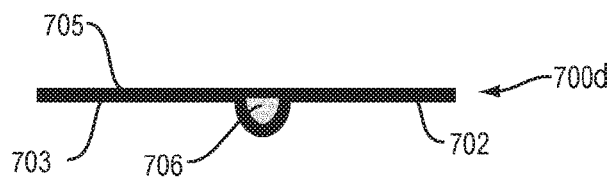
FIG. 7C                FIG. 7D

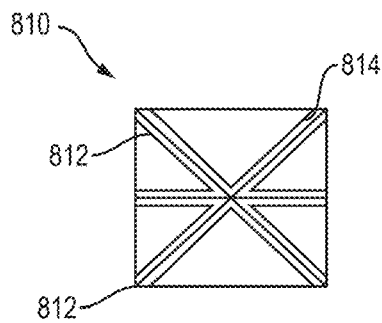
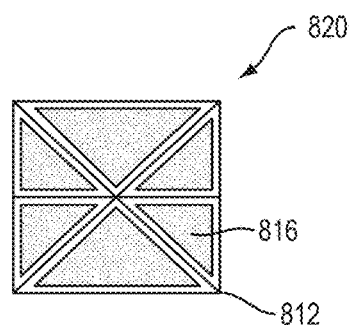
FIG. 8A  FIG. 8B
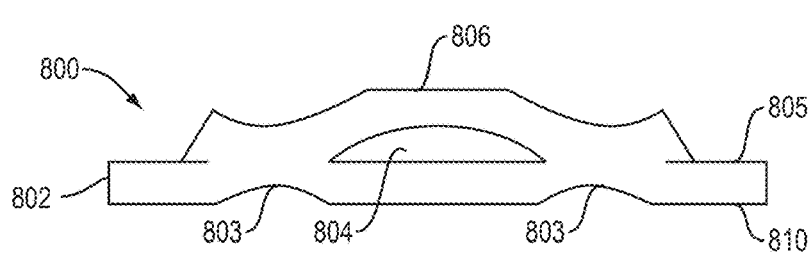
FIG. 8C
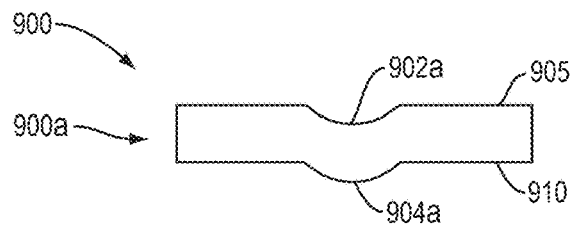
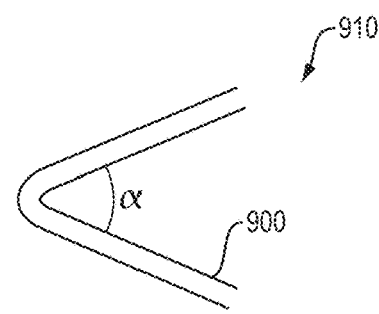
FIG. 9A  FIG. 9B
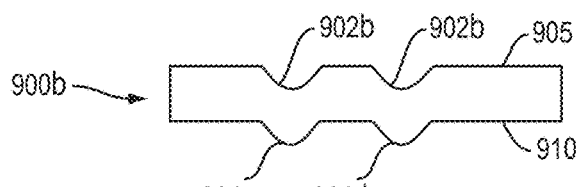
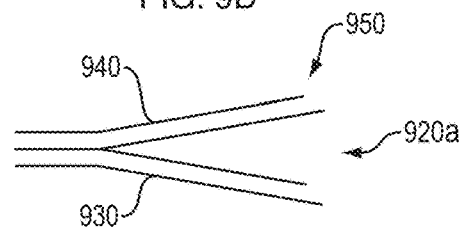
FIG. 9C  FIG. 9D
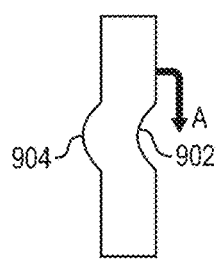
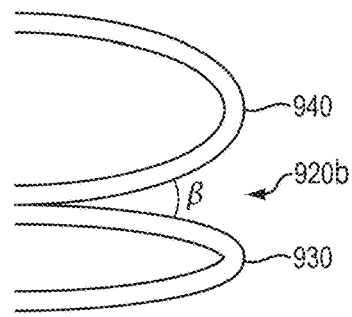
FIG. 9E  FIG. 9F

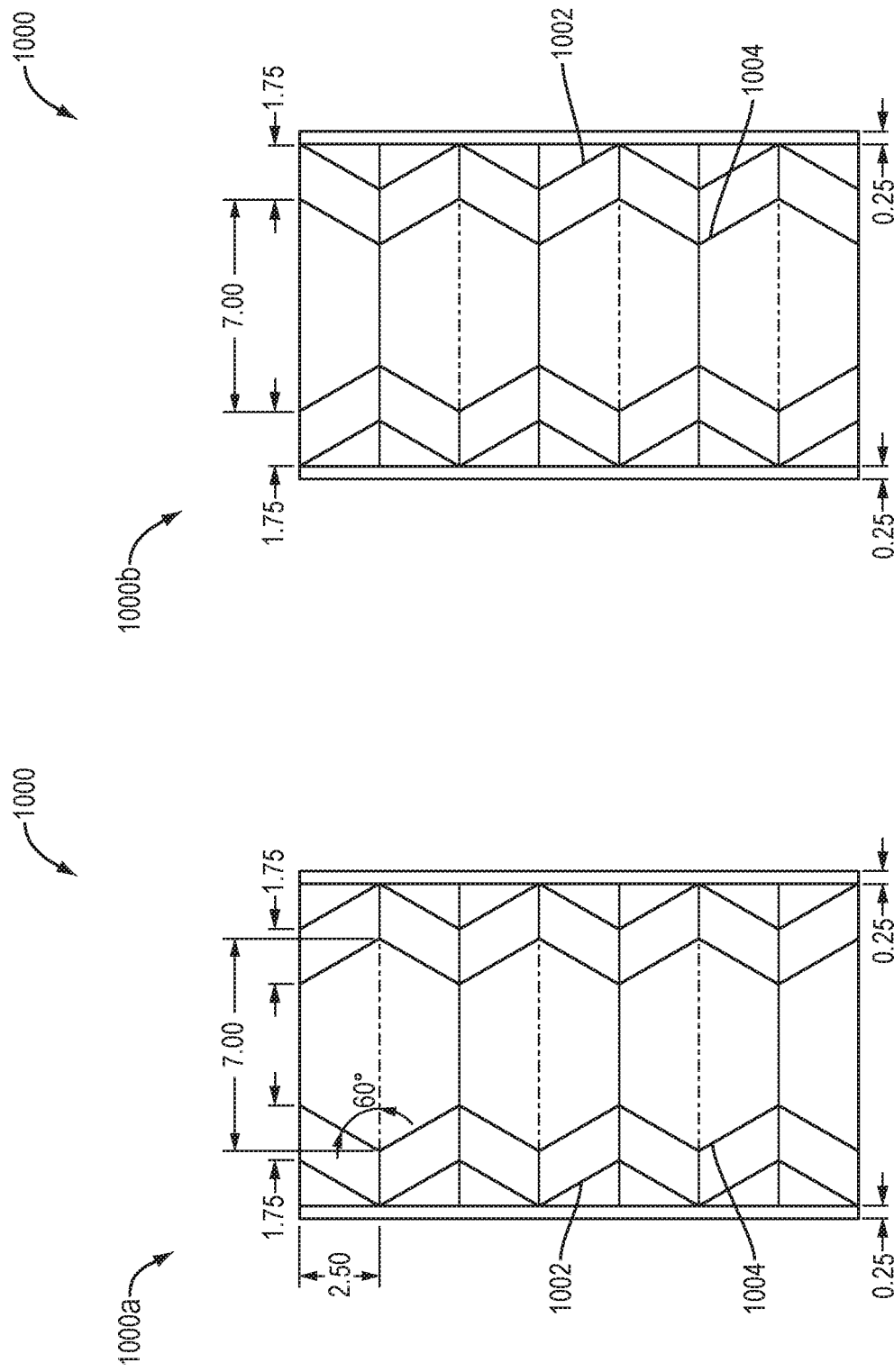

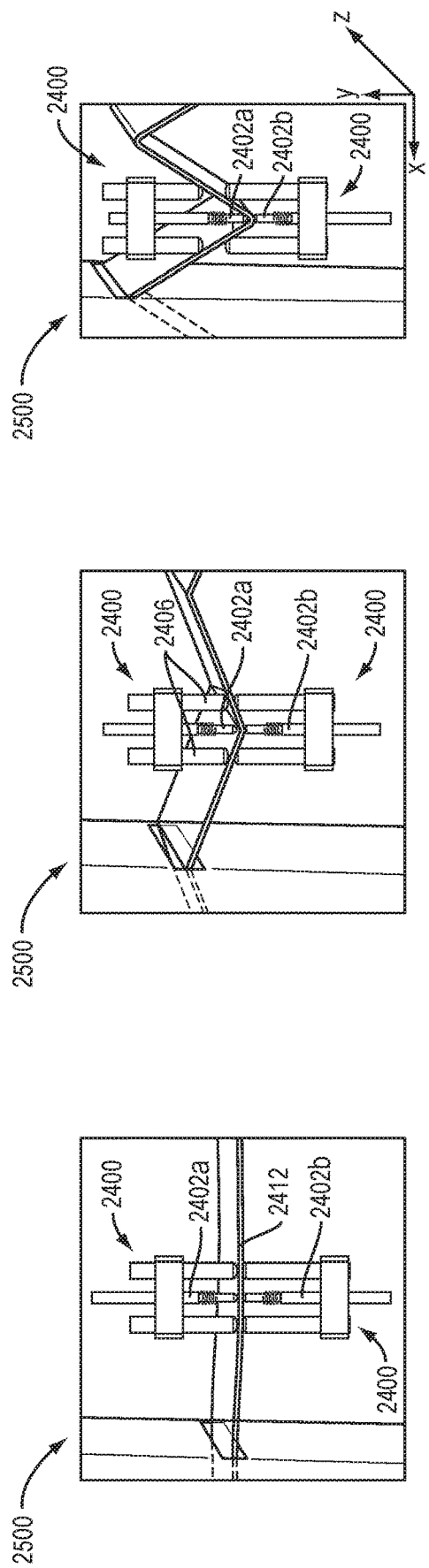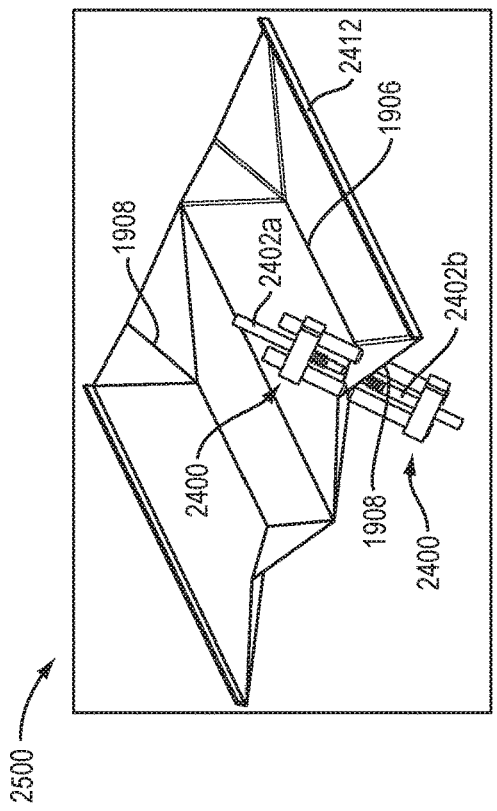

ARTICULATING BIOCONTAINERS

RELATED APPLICATIONS

The application is a U.S. National Stage application of International Application No. PCT/US2020/049846, filed Sep. 9, 2020, which claims the benefit of priority to U.S. Provisional 62/898,402, dated Sep. 10, 2019, each of which is incorporated by reference in its entirety.

FIELD OF THE DISCLOSURE

This disclosure relates to biocontainers and bags for bioprocessing operations. More particularly, embodiments of the biocontainers and bags described within the disclosure relate to structures comprising films that can collapse and articulate in predictable manners.

BACKGROUND

The use of single use bioreactors, bags, and other biocontainers is growing in the bioprocessing industry. These bioreactors, bags, and biocontainers, which comprise films, come into contact with biological fluids. Therefore, bioreactors, bags, and biocontainers replace stainless tanks in that biological fluids need not contact the steel, which is difficult and expensive to clean and sterilize. Totes and bins for the storage and transportation of liquids and solids such as raw materials, intermediates, and finished goods, are also expensive. Processes include cell culturing and other bioprocessing, such as the production of desired products, e.g., the inactivation of viruses for use in plant and animal-based cells.

Bags are typically manufactured from multilayered plastic film laminates and are generally bulky. Typically, laminates include four or more film regions (generally between 4 and 10 sheets). The sheets have, at least, an inner sheet having a surface that is in contact with the liquid or solid within the bag and an outer sheet or laminate. The inner sheet comprises multiple films and comprises a generally inert material having low extractables, such as polyethylene, which is specified for chemical resistance and strength. An outer sheet provides support, burst resistance, strength, and some measure of protection to the remaining sheets of the biocontainer, which is generally formed of one or more plastic films, such as polyethylene, polypropylene, polyethylene-vinyl acetate (EVA), polyethylene terephthalate (PET), polyamide (nylon), and the like. At least one barrier sheet is disposed between the inner sheet and the outer sheet, which often has one or more gas impermeable films, such as polyethylene vinyl acetate, polyethylene vinyl alcohol (EVOH), and the like. An additional outer strength sheet, typically comprising a thick fabric substrate, is normally disposed on the outer sheet. The barrier sheet may be laminated with the first inner sheet or the outer sheet. The gas impermeable film(s) are formed of plastic materials which tend to be crystalline and are, accordingly, brittle and/or susceptible to cracking and/or crazing.

Past bags are formed from diecut, outfitted panels, consisting of sheet materials, that are welded together. The bags are inflated with air and integrity tested. Following testing, the bags are folded by a technician. However, folding the bag in a desired design is highly dependent upon the talent and experience of the technician. Moreover, bags have different designs and may be formed of different polymeric materials and/or have different or variable thicknesses. Accordingly, the bags cannot be repeatably folded or compacted, resulting in unpredictable creasing, i.e., leading to quality problems. The folding, handling and manipulation of the bag or biocontainer, during testing, packing, unpacking, and/or use in bioprocessing stresses the films and leads to the formation of defects, e.g., stress concentrations and cracks. These cracks tend to propagate and spread through as intra-layer cracks and inter-layer cracks, eventually compromising and, in turn, damaging the biocontainer. These damaging breaches cause leaks and a loss of sterility within an inner volume of the bag or biocontainer, resulting in losses in biological products. Therefore, biocontainer and bag product returns and/or loss of biological products become prohibitively expensive. Furthermore, bioreactors, bags, and biocontainers, and in particular larger sizes, e.g., greater than 200 L, cannot standalone and must be housed with a strong shell (such as a stainless-steel shell).

A new biocontainer, bag, liner, and/or bioreactor that is resistant to stress concentrations and cracks, while remaining thin and flexible, which articulates along specified joints and, optionally, can standalone without supporting apparatus would represent an advance in the art.

SUMMARY OF SOME EMBODIMENTS

Biocontainers according to some embodiments of the disclosure comprise zones or articulation and zones of non-articulation to create articulated joints. In some embodiments, the biocontainers have strength and/or rigidity capable of being a standalone biocontainer, having little to no surrounding support structure, i.e., no surrounding shell is necessary. In some embodiments, the biocontainers have strength and/or rigidity capable of being a standalone biocontainer, can maintain an expanded state without the support of a secondary container, permitting a system having reduced footprint compared with supported systems. In some embodiments, the biocontainer has significantly greater flexural endurance, i.e., can be folded/compacted, expanded, folded/compacted, and expanded multiple times without failure. In some embodiments, articulations can be designed for optimal locations for differing biocontainers, e.g., differing folding pattern(s), and/or differing tessellation to ensure bending occurs at the point of articulation, wherein uncontrolled bending or creasing at random locations is reduced. In some embodiments, differing folding pattern(s) permit great compaction and/or deployment. In some embodiments, the articulated joint(s) presets a bend radius into the material at conditions where the material strength is minimally impacted such that when the material is folded at a preset articulated bend radius, the stress to the sheet is minimized. In some embodiments, folding and unfolding of the bag will preferentially follow paths of least resistance, i.e., folding radii which are pre-installed into the material, making articulated joints, in a designed pattern, create paths of lower resistance to bending, reducing the likelihood of random flexing and/or creasing. The biocontainers contemplated herein may be a 2-dimensional (2D) or a 3-dimensional (3D) biocontainer capable of storing biological fluids. Some embodiments of the disclosure are made of two pieces or panels of film. Some embodiments of the disclosure are made of three to ten pieces or panels of film, which can be joined by the various methods disclosed herein. Some embodiments of the biocontainers herein comprise flexible films that form a closed volume for containing biological fluids. It is further contemplated that some embodiments of the disclosure comprise flexible films that are stiffer than convention flexible films used in the manufacture of biocontainers. It is further contemplated that some embodiments of the disclosure comprise flexible ports and/or flexible fluid channels.

In some embodiments, biocontainers can maintain their shape once filled with biological fluids and require minimal to no support to prevent tipping. In some embodiments, the incorporation of "double-jointed" articulation produces joints having flexibility in two directions, wherein combining double-jointed articulation with patterns that allow for folding in one direction and locking upon deployment in an opposite direction. In some embodiments, rigidity of the biocontainers can be further improved by constructing stiffer non-articulated zones, e.g., creating zones of differing stiffness by changing the thickness of the material in one or more zones, using a stiffer material in differing zones, and/or changing materials of construction in differing zones.

In some embodiments, different panels having different thicknesses are used to create articulation joints. In some embodiments, differences in thicknesses at zones are created by thinning the cross section of the film. In some embodiments, differences in thicknesses at zones are created by thickening the cross section of the film. In some embodiments, differences in thicknesses at zones are created by thinning and thickening the cross section of the film, e.g., mountains and valleys. Thinned areas may be created by, for example, directionally heating one side of a film but not the other. Thinned areas may also be created by, for example, directionally etching, scoring, and/or ablating on side but not the other of a film. Directional pressures may also be employed to thin various areas on a film.

In some embodiments, thickening of the films is employed. Paths for articulation by adding thickness to either side of designed articulation path(s) can be accomplished by adding material to areas not intended to articulate, wherein a stiffening occurs, thereby creating an articulation path along an adjacent area without added thickness. Thickening steps can be combined with other articulation methods described herein. Methods of producing thickened areas include, but are not necessarily limited to, adhering (via adhesives and/or thermal bonding) panels of material to a film. Adhering material to an articulated area, such as a polymeric material and/or adding, embedding or encapsulating a rod-shaped material, whether polymeric, filaments, or metallic along a path.

Some embodiments disclosed herein provide a material formed of a film having one or more contact layers on its inner surface and one or more layers of a gas impermeable polymer resin on its outer surface and a substrate incorporated between the inner contact and outer impermeable layers wherein the substrate is formed of a fibrous material selected from the group consisting of woven fibrous material selected from the group consisting of a material selected from the group consisting of polymers, metal fibers, glass fibers, and carbon fibers.

Some embodiments disclosed herein provide a biocontainer formed of any, all, or selected combinations of the films or materials above and herein. Some embodiments disclosed herein provide a biocontainer comprising single films that are scored or ablated using heat and/or pressure, and or the heat-sealing of multiple films and/or the addition of polymeric structures to creates articulating elements. The term articulated elements herein includes the terms articulations, articulating, and the like and are used interchangeably. The term articulation is intended to indicate an area of a film that preferentially bends or folds compared at the articulation as compared with non-articulated areas.

These and other provisions will become clear from the description, claims, and figures below. Various benefits, aspects, novel and inventive features of the present disclosure, as well as details of exemplary embodiments thereof, will be more fully understood from the following description and drawings. So the manner in which the features disclosed herein can be understood in detail, more particular descriptions of the embodiments of the disclosure, briefly summarized above, may be had by reference to the appended drawings. It is to be noted, however, that the appended drawings illustrate only typical embodiments of this disclosure and are therefore not to be considered limiting of its scope, for the described embodiments may admit to other equally effective bags, biocontainers, films and/or materials. It is also to be understood that elements and features of one embodiment may be found in other embodiments without further recitation and that, where possible, identical reference numerals have been used to indicate comparable elements that are common to the figures. As used herein, the singular forms "a," "an," and "the" include plural referents unless the context dearly dictates otherwise. Unless defined otherwise, all technical and scientific terms used herein have the same meaning as commonly understood by one of ordinary skill in the art to which these embodiments pertain. Also, the following terms used herein are subject to the following definitions, unless the context indicates otherwise.

BRIEF DESCRIPTION OF THE FIGURES

FIGS. 3A-3B depict a cross section of a film having a double articulation according to a third embodiment of the present disclosure;

FIG. 4 depicts a film having material added opposite a thinned or bowed path, according to a fourth embodiment of the present disclosure;

FIG. 5 depicts a film having material added adjacent to a channel, according to a fifth embodiment of the present disclosure;

FIGS. 6A-6B depict a film having material added on an external surface or within a preformed channel, according to a sixth embodiment of the present disclosure;

FIGS. 7A-7D depict a film having rod-like members embedded within a film, according to a seventh embodiment of the present disclosure;

FIGS. 8A-8C depict a film comprising a fluid or gas pathway disposed between a base film and a second film, according to embodiments of the disclosure;

FIGS. 9A-9F depict a film having a channel on a first surface of the film and a protrusion on a second surface opposite the first surface, according to a ninth embodiment of the present disclosure;

FIGS. 10A-10B depict a Tachi-Miura polyhedron having a pattern of pathways formed therein, according to embodiments of the disclosure;

FIGS. 25A-D depict a process for making, for example, the panels for making the biocontainer, a four-plane tessellated biocontainer, according to embodiments of the disclosure;

DETAILED DESCRIPTION OF THE DISCLOSURE

The term film within the meaning of this disclosure means any flexible material that is capable of being fused with another flexible film, including, but not limited to, polymeric sheet, composites, laminates, single-layer, and/or multi-layer polymeric materials. These films may further comprise substrates, which may comprise plastics netting, wovens, non-wovens, knits, and/or metallic foils and other flexible structures and materials. In some embodiments, the flexible films comprise a laminate film structure with a lower melting point material internal to an external higher melting point polymer. Also, in some embodiments, the flexible films comprise a laminate film structure with a lower melting point material surrounding a higher melting point woven, knit, or non-woven material.

The term biocontainer is defined broadly as any flexible container or vessel capable of holding a fluid within an internal volume or region, and may be in the form of a two-dimensional, three-dimensional, and/or multi-faceted bag or bioreactor.

Figure 1A:
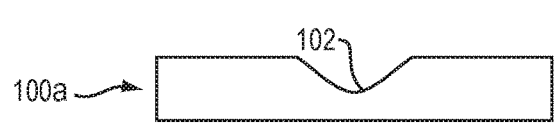
FIGS. 1A-1F depict a cross section of a film having a thinned path according to a first embodiment, according to the present disclosure.
Figure 1B:
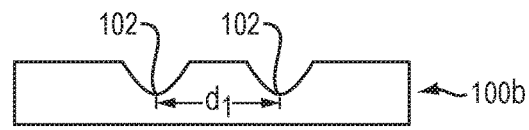

FIGS. 1A-1F depicts a cross section of a film having a thinned path according to a first embodiment, according to the present disclosure. FIG. 1A depicts a cross section of a film 100a having a thinned path 102, according to a first embodiment of the present disclosure. The thinned path 102 is reduced in thickness by approximately 30-70% of the total thickness of the film 100a. In some embodiments, the thinned path 102 is present on one side of the film 100a. The radius of curvature of the thinned path 102 is dependent on the thickness of the film resulting in approximately 30-<180° of curvature. In this context, the curvature represents, for example, a radius of a tool used to impart the thinned path 102. It is contemplated that a circular tool having a radius equal to the thickness of the film 100a could be used, using heat and/or pressure, to score or ablate the thinned path 102 into the film 100a (and the other films described herein). It is to be understood that tools having non-circular geometries may be used to score or ablate the film 100a. The thinned path 102 may have a depth, for example, of 30-70% of the total thickness of the film 100a. In some embodiments, the path may be a scoring or ablation, i.e., plastic is removed from the film 100a. In some embodiments, the plastic is displaced, i.e., a heated tool melts and moves plastic to create a path or trough having a peak(s) adjacent to the path within the film 100a. In some embodiments, the path may be created by both removing plastic material and by displacing plastic material. In some embodiments, the removal of plastic material and the displacement of plastic material is performed in a single operation. FIG. 1B depicts a cross section of a film 100b having two thinned paths 102, according to a second embodiment of the present disclosure. The thinned paths 102 are reduced in thickness by approximately 30-70% of the total thickness of the film 100b. The radius of curvature of the thinned path 102 is dependent on the thickness of the film resulting in approximately from 30-≤180° of curvature. The distance $d_1$ between the two thinned paths 102 ranges from approximately 1× the smallest to 3× the largest of the radii of curvature of the thinned paths 102. In some embodiments, the thinned path 102 is present on one side of the film 100b.

Figure 1C:
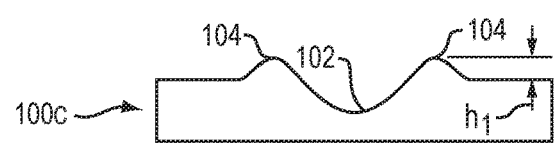
Figure 1D:
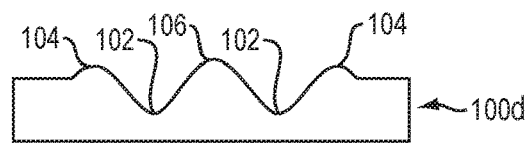
Figure 1E:
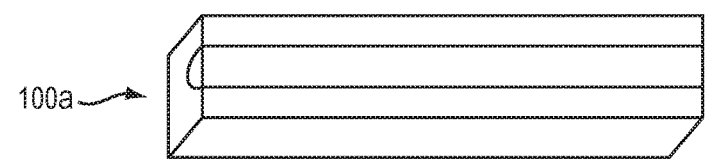
Figure 1F:
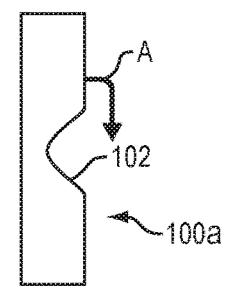

FIG. 1C depicts a cross section of a film 100c having a thinned path 102, according to a third embodiment of the present disclosure. The thinned path 102 is reduced in thickness by approximately 30-70% of the total thickness of the film 100c. The radius of curvature of the thinned path 102 is dependent on the thickness of the film resulting in approximately 30-<180° of curvature. The cross section of the film 100c also comprises rails 104 on the periphery of the thinned path 102. In some embodiments, the thinned path 102 and rails 104 are present on one side of the film 100c. The rails 104 can be formed, for example, by a heated tool that melts the film 100c, bunching up the plastic of the film. FIG. 1D depicts a cross section of a film 100d having two thinned paths 102, according to a fourth embodiment of the present disclosure. The thinned paths 102 are reduced in thickness by approximately 30-70% of the total thickness of the film 100d. The radius of curvature of the thinned path 102 is dependent on the thickness of the film resulting in approximately 30-≤180° of curvature. The distance $d_1$ between the two thinned paths 102 ranges from approximately 1× at the smallest to 3× the largest of the radii of curvature of the thinned paths 102. The cross section of the film 100d also comprises rails 104 on the periphery of the thinned path 102 and a third rail 106 disposed therebetween. The rails 104 have a height $h_1$. The height $h_1$ is approximately 15-40% of the original thickness. In some embodiments, the thinned path 102 and rails 104, 106 are present on one side of the film 100d. FIG. 1E depicts a perspective view of the film 100a. FIG. 1F depicts a side view of the film 100a, having a thinned path 102 and demonstrating a direction of articulation A. FIG. 1F also depicts a perspective view of the film 100a, having a thinned path 102.

Figure 2A:
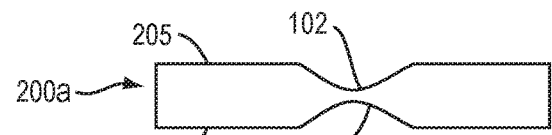
FIGS. 2A-2F depict a cross section of a film having at least one thinned path on opposite surfaces, according to a second embodiment of the present disclosure.
Figure 2B:
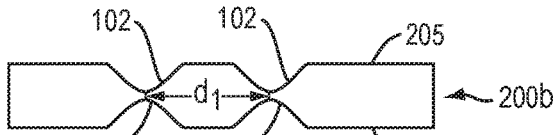

FIGS. 2A-2F depicts a cross section of a film having at least one thinned path on opposite surfaces, according to a second embodiment of the present disclosure. FIG. 2A depicts a cross section of a film having at least one thinned path 102 on opposite surfaces 205, 210, according to a second embodiment of the present disclosure. For example, as shown in the cross section of a film 200a, a thinned path 102 is within a first surface 205 and a second thinned path 102 is within a second surface 205, which is opposite the first surface 205. As depicted, the thinned path 102 within the first surface 205 is directly opposite the thinned path 102 within the second surface 210, although this is optional and an offset regarding the location of the two thinned paths 102 are within the scope of the disclosure. As above, the thinned path 102 is reduced in thickness within the film 200a by approximately 30-70% of the total thickness of the film 200a. The radius of curvature of the thinned path 102 is dependent on the thickness of the film resulting in ranges from approximately 30-180° of curvature. FIG. 2B further depicts a cross section of a film 200b having two thinned paths 102 on each of surfaces 205, 210. The thinned paths 102 together reduce the thickness by approximately 30-70% of the total thickness of the film 200b. The radius of curvature of the thinned path 102 is dependent on the thickness of the film resulting in approximately 30-<180° of curvature. The distance $d_1$ between the two thinned paths 102 ranges from approximately 1× the smallest to 3× the largest of the radii of curvature of the thinned paths 102.

Figure 2C:
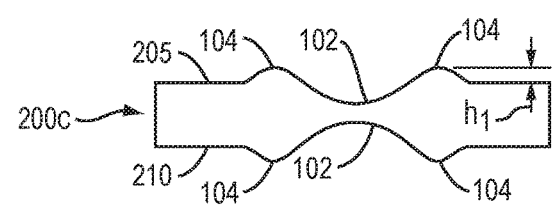
Figure 2D:
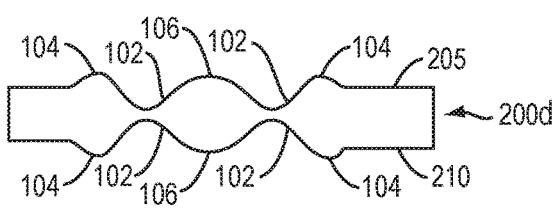
Figure 2E:
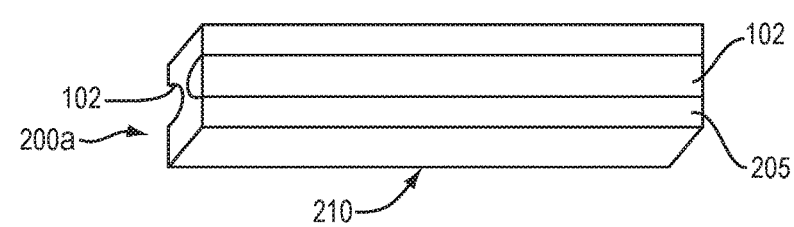
Figure 2F:
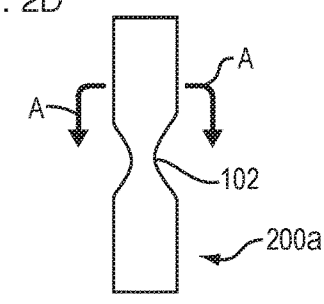

FIG. 2C depicts yet another cross section of a film 200c having at least one thinned path 102 on opposite surfaces 205, 210, as described above. As shown in the cross section of a film 200c, a thinned path 102 is within a first surface 205 and a second thinned path 102 is within a second surface 205, which is opposite the first surface 205. As above, the thinned path 102 within the first surface 205 is directly opposite the thinned path 102 within the second surface 210, although this is optional and an offset regarding the location of the two thinned paths 102 are within the scope of the disclosure. The thinned path 102 is reduced in thickness by approximately 30-70% of the total thickness of the film 100c. The radius of curvature of the thinned path 102 is dependent on the thickness of the film resulting in approximately 30-<180° of curvature. As shown, the film 200c comprises rails 104 on the periphery of the thinned paths 102 on both surfaces 205, 210. The rails 104 have a height $h_1$. The height $h_1$ ranges from approximately 0-40% of the original thickness. In other words, it is possible that ablation will leave no rails remaining. FIG. 2D further exemplifies another embodiment, according to the disclosure, of a film 200d. The cross section of the film 200d also comprises rails 104 on the peripheries of the thinned paths 102 and a third rail 106 disposed therebetween on surfaces 205, 210 of the film 200d. The rails 104 have a height $h_1$, as described above. The height $h_1$ is approximately 0-40% of the original thickness. FIG. 2E depicts a perspective view of the film 200a having thinned paths 102 on two opposing sides. FIG. 2F depicts a side view of the film 200a, having a thinned path 102 and demonstrating two possible directions of articulation A. FIG. 2F also depicts a perspective view of the film 200a, having a thinned path 102 within the surface 205 (top) and a thinned path 102 within the surface (bottom) 210.

FIGS. 3A-3B depicts a cross section of a film having a double articulation according to a third embodiment of the present disclosure. FIG. 3A depicts a cross section of a film 300 having a double articulation according to a third embodiment of the present disclosure. In some embodiments, the film 300 may comprise a plurality of articulations, e.g., three, four, five . . . n paths 102, 104. It is to be understood that additional articulations produce additional flexibility. Nonetheless, it is contemplated that the film 300 may comprise one articulation. A film 300 a comprises a bowed path 102 and an opposing bowed path 104 on a surface 205, resulting in a bowed path 102 and an opposing path 104 on surface 210. In this context, a bowed path 102 indicates that the thickness of the film 300 will have changed very little or none at all. In other words, the use of a heated tool and pressure, and, optionally, a table having a surface with a pathway disposed therein on which the film 300 sits, can move the plastic material into the bowed path 104 without removing any of the plastic film 300. The bowed path 102 and the opposing bowed path 104 are offset by a distance d2 (from 1× the smallest to 3× the largest radii of curvature), creating a double articulation (or triple, quadruple, etc.). FIG. 3B also depicts a film 300 b, having a double articulation, according to the present disclosure. The film 300 b comprises a bowed path 102 and an opposing bowed path 104 on a surface 205 resulting in a bowed path 102 and an opposing bowed path 104 on a surface 210. In this embodiment, however, the film 300 b has no inflection point disposed between the thinned path 102 and the rail 104. In other words, there is no distance d1 between the thinned path 102 and the rail 104. In some embodiments, the bowed path 104 comprises a radius that is large, e.g., larger than the thickness of the underlying film. The double articulation may be disposed on a film in a pattern that allows for folding in one direction and locking upon deployment in an opposite direction.

FIG. 4 depicts a side view of a film 400 having material added opposite a thinned or bowed path 102, according to a fourth embodiment of the present disclosure. As shown, path 102, which may be a thinned path as described above or a bowed path as described above, is within the surface 210 and a strip 402 adhered to a surface 205. As shown, the strip 402 comprises a concave surface 404. In practice, the strip 402 may also have a convex shape (not shown) for added strength and/or stiffness. The strip has a height $h_2$, from the surface 205 to the top of the strip 402. The height $h_2$ ranges from approximately ½× to 3× the original film thickness, which controls the height $h_3$ (or thickness) of the film 400 between the thinned path 102 and the concave surface 404 of the strip 402. As shown, the radius of curvature of the thinned or bowed path 102 and the concave surface 404 of the strip 402 are substantially equal. It is also contemplated herein that where the curvature of radii are different, a slightly lesser or a slightly more articulation may be created. Also, as shown, the strip 402 is wider than the thinned path 102, which can also create differences in stiffness. The distance $d_3$ between the thinned paths 102 on the surface 210 ranges from approximately 3 mm to approximately 30 mm. As shown, there is no difference in thickness over the length of $d_3$ and, accordingly, no (or little) articulation in this area. It is to be understood that the strips 402 add stiffness in the z direction. In other words, the film 400 is substantially restricted from bending, or otherwise articulating except where desired.

FIG. 5 depicts a film 500 having material added adjacent to a bowed path 102, according to a fifth embodiment of the present disclosure. FIG. 5 comprises a bowed path 102a.

The bowed path 102a has a height between h₄. The height h₄ is substantially the same as the thickness of the film 500, as evidenced by the distance between the surface of 102a and a surface 103. Accordingly, the film 500 comprises an articulation A in the direction shown, which is between the strips 402.

FIGS. 6A-6B depicts a film having material added on an external surface or within a preformed channel, according to a sixth embodiment of the present disclosure. FIG. 6A depicts a film 600 having material added on an external surface 606 or within a film 601 having a preformed bowed path 602, according to a sixth embodiment of the present disclosure. As shown, a film 600a comprises a film 601 and a preformed bowed path 602. The film 601, although bowed, has a substantially similar thickness, i.e., the cross section of film 601 is similar where bowed and where not bowed. Disposed on the external surface 606 of the preformed path 602 is an additional material 604. FIG. 6B depicts a film 600b comprising a film 601 having a preformed path 602. In some embodiments, the preformed bowed path 602 comprises an additional material, here an additional material 607, disposed thereon. In some embodiments, the additional material 607 is itself a film. The additional material 604, 607 adds thickness in some areas to the film 601. In some embodiments, the film 601 is thicker than the additional material 604 or films 601 added on the preformed paths 602. In some embodiments, the films 601 is thinner. Differing thicknesses of the films 601, additional materials 604, and additional materials 607 can create articulations of different, and desirable, strengths. The additional material(s) may comprise a polymeric film.

FIGS. 7A-7D depicts a film having rod-like members embedded within a film, according to a seventh embodiment of the present disclosure. FIG. 7A depicts films 700 having rod-like members 704, 706, 708 embedded within the film 702, according to a seventh embodiment of the present disclosure. The film 700a comprises a film 702 having a rod-like member 708 embedded therein. As depicted, the film 702 traverses through the center of the member 708. FIG. 7B depicts a film 700b comprising a film 702 having a rod-like member 708 embedded therein, the rod-like member 708 may be a metal, a plastic, a monofilament or fiber, and/or the like. As depicted, the film 702 traverses a distal edge or arc of the member 708. It is to be understood that a side 703 or a side 705 can be an inner side, i.e., the side that contacts a biological fluid, of a biocontainer formed therewith. Conversely, the side 703 or the side 705 can be an outer side of a biocontainer formed therewith. FIG. 7C depicts a film 700c comprising a film 702 having a cylindrical member 704 embedded therein. The cylindrical member 704 comprises a hollow fiber or hollow tube. As depicted, the film 702 traverses a distal edge or arc of the member 704. FIG. 7D depicts a film 700d comprising a film 702 having a solid, semi-circular rod-like member 706 embedded therein. As depicted, the film 702 traverses a distal edge of the member 706. As with the films 700a, 700b, the films 700c and 700d also comprise sides 703, 705, which may be disposed on an inner side of a biocontainer or an outer side of a biocontainer formed therewith.

FIGS. 8A-8C depicts a film comprising a fluid or gas pathway disposed between a base film and a second film, according to embodiments of the disclosure. FIG. 8A depicts a cross section view of a film 800 comprising a fluid or gas channel or pathway 804 disposed between a base film 802 and a second film 806, according to embodiments of the disclosure. The fluid pathway 804 may comprise liquids, gels, dispersions, air, another gas, or mixtures thereof. As depicted, the film 800 comprises two articulation paths 803 disposed within an edge 810, wherein the pathway 804 is disposed therebetween an edge 805, opposite the edge 810, of the base film 802 and the second film 806. The articulation paths 803 can comprise any of the paths described herein. Other embodiments of the film 800 are possible. For example, a third articulation path may be disposed under the channel or pathway 804 (not shown). Similarly, the two thinned paths 803 may be removed and only one thinned path may be situated below the pathway 806, wherein a fluid pathway for imparting stiffening or flexibility is created. In some embodiments, the second film 806 has an underlying articulation path (for dual function in the pathway), which is laminated with the base film 802 to form the pathway 804 therebetween. The film 800 can be used to form a film 810 having patterns 812. Areas between the pathways 812 additionally can be articulated. And, the paths for articulation can be inflated with air or any other gaseous or liquid fluid. Alternatively, as in FIG. 8B, the strips 812 can be surrounded by panels 816 in a film 820. Any of the articulation or stiffening paths can be inflated, so the outer pathways could be both articulation points as well as stiffening points and the inner path could also be a combined articulation/inflation pathway. Pathways may be formed by sealing, e.g., laminating, two pieces of sheet or film so that a pocket of space is formed therebetween. These pathways can be inflated to create an articulation, i.e., a bend in the film, to stiffen a joint once deployed, to stiffen a panel to avoid unwanted bending. Inflation of such pathways can assist in the compaction and/or deployment of biocontainers formed therewith. Inflation of such pathways can also assist in stiffening the biocontainer, promoting a status of being self-standing once deployed.

FIGS. 9A-9F depicts a film having a channel on a first surface of the film and a protrusion on a second surface opposite the first surface, according to a ninth embodiment of the present disclosure. FIG. 9A depicts a front section view of a film 900a having a channel 902a on a first surface 905 of the film 900a and a protrusion 904a on a second surface 910 opposite the first surface 905, according to a ninth embodiment of the present disclosure. As shown, the channel 902a and the protrusion 904a have approximately a similar radius of curvature. The films 900, such as films 900a, 900b, can be used to create the articulation 910. As shown, the articulation 910, as depicted in FIG. 9B, is a hinge. A hinge can be created by folding the film 900 using heat and/or pressure. The hinge 910, made using a single film, is a versatile construction because although the hinge 910 is permanent (as would be made using heat and/or pressure), the hinge 910 can articulate from very small angles α 5° to nearly 180°. By way of comparison, a sealed joint 950 comprises a first film 940 sealed, e.g., heat-sealed, calendared, or adhesive bonded with a second film 930. As depicted, in 920a, as in FIG. 9D, before articulation, the films 940 and 930 have a slight angle between them. As shown in the film 920b, as in FIG. 9F, the angle β for articulation is less than 90°. It is to be noted that films 940 and 930 can be any of the films discussed herein, i.e., film 100a, 100b, 100c, 100d, 200a, 200b, 200c, 200d, 300a, 300b, 400, 500, 600a, 600b, 700a, 700b, 700c, 700d, 800, 900a, 900b, 1000a, 1000b, 1102, 1202, 1402, 1600a, and others.

FIG. 9C depicts a front section view of a film 900b having a plurality of channels 902b on a first surface 905 of the film 900b and a plurality of protrusions 904c, 904d on a second surface 910 opposite the first surface 905, according to the present disclosure. It is to be understood that the plurality of protrusions 904c, 904d need not have the same radius of curvature. For example, by way of example, a protrusion 904c having a larger radius of curvature would embody more of the material of which it is formed and therefore be concomitantly stiffer, allowing designers to create varied articulations, such as Articulation A. Also, it is to be understood that the radius if curvature of the protrusions 904c, 904d need not be the same as the corresponding channels 902b. FIG. 9F depicts a side view of a film, such as the film 900a, having a thinned path 902a and a projection 904a and demonstrating a direction of articulation A.

FIGS. 10A-10B depict a Tachi-Miura polyhedron having a pattern of pathways formed therein, according to embodiments of the disclosure. FIG. 10A depicts Tachi-Miura polyhedron films 1000 having a pattern of pathways 1002, 1004 formed therein, according to embodiments of the disclosure. Two Tachi-Miura polyhedrons 1000a, 1000b are shown. The dimensions shown are in inches. A valley fold, e.g., 1002, is formed by folding the film forward into itself. A mountain fold, e.g., 1004, is the opposite of a valley fold, i.e., the film is folded to its opposite side. Because the mountain fold is the opposite of the valley fold, turning the film over produces a valley fold. The mountain folds and valley folds are any type of the articulation paths, channels, etc., as described herein. For example, the mountain folds and valley folds may be formed by a heated roller, e.g., directional heating. The heated roller comprises a pattern. In some embodiments, the pattern produces a continuous path, e.g., non-interrupted. In some embodiments, the bowed path and/or the thinned path is a discontinuous or discontiguous path. Some embodiments of the disclosure start with a sheet of film that is, e.g., 0.008" to 0.012" in thickness (0.200 mm to 0.300 mm). The heated roller creates the thinned pathways, e.g., valley folds 1002 and mountain folds 1004. In other words, the original thickness is reduced to, e.g., 0.15 mm. Accordingly, thinned pathways that are from approximately 60-80% of the original thickness are possible. It is to be understood that films having a thickness outside the previous range are within the scope of this disclosure, i.e., 0.100 mm or 0.400-0.500 mm. The films 1000a (as in FIG. 10A), 1000b (as in FIG. 10B) can be folded and/or joined with other films described herein to create articulating biocontainers. Heat sealing is a suitable method as many adhesives can produce volatile organic compounds and/or extractables, which can be harmful to cells within biological fluids. For example, one piece of film 1000a can be joined, as a front piece, with one piece of film 1000b, as a back piece, to form an articulating biocontainer.

Figure 11:
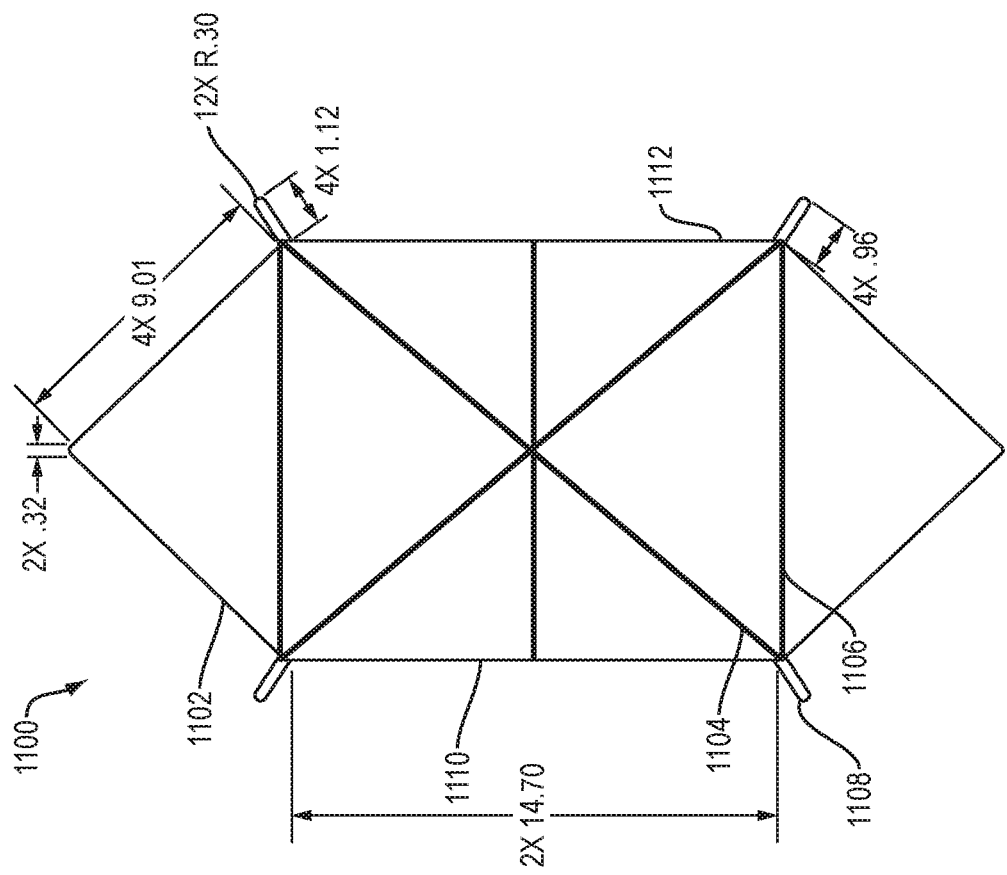
FIG. 11 depicts a side view of a film in the form of a modified balloon fold, according to embodiments of the disclosure.

FIG. 11 depicts a side view 1100 of a film 1102 in the form of a modified balloon fold, according to embodiments of the disclosure. The film 1102 has a first side 1110 and a second side 1112 opposite the first side 1110. The film 1102 has channels 1104 disposed therein, as described above. In some embodiments, the channels 1104 are valley folds and the channels 1106 are mountain folds. In some embodiments, the film 1102 comprises tabs 1108, which can assist in aligning the panels or films before welding or heat sealing. As above, various pieces of the films 1102 may be joined together to form articulating biocontainers. For example, the film 1102 can be side panels that are joined with front and back panels, described below.

Figure 12:
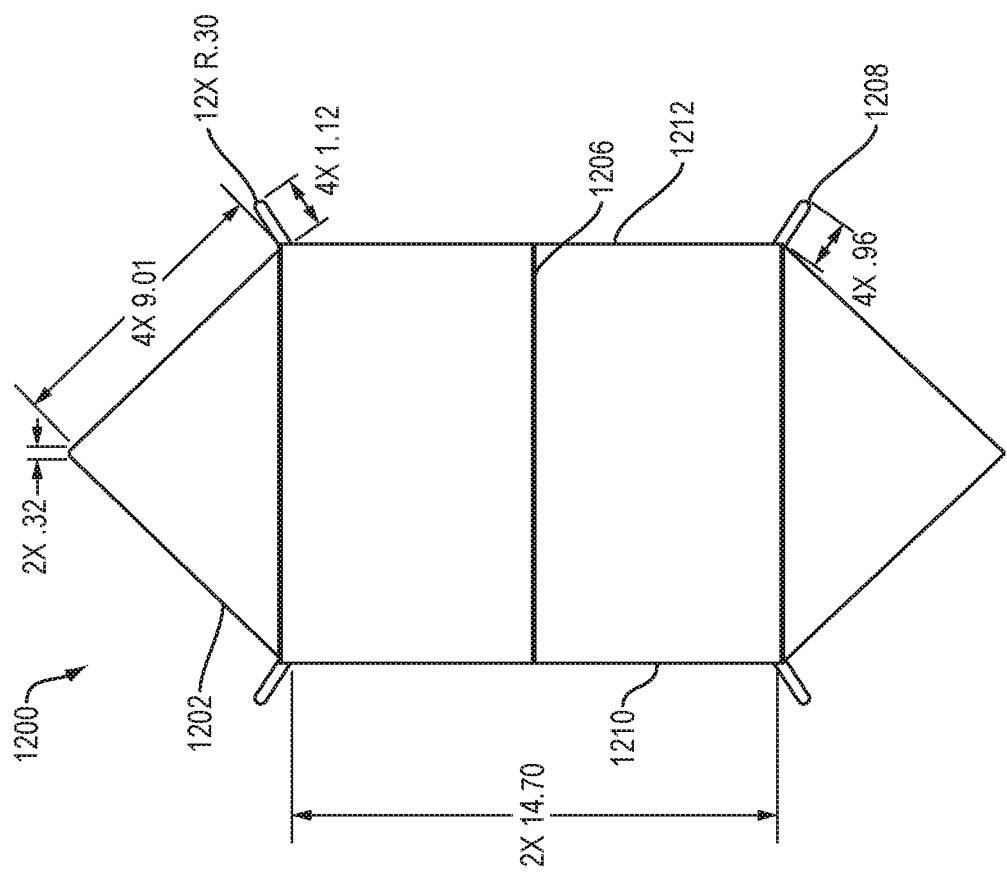
FIG. 12 depicts a side view of a film in the form of a modified balloon fold, according to embodiments of the disclosure.

FIG. 12 depicts a side view 1200 of a film 1202 in the form of a modified balloon fold, according to embodiments of the disclosure. The film 1202 has a first side 1210 and a second side 1212 opposite the first side 1210. The film 1202 has channels 1206 disposed therein. In some embodiments, the channels 1206 are mountain folds. The channels 1204 may further comprise any of the articulated pathways described herein, such as by folding with heat and pressure or scoring, ablating, etc. The film 1202 can be used, for example, as front and back panels in conjunction with the side panels, discussed above.

Figure 13:
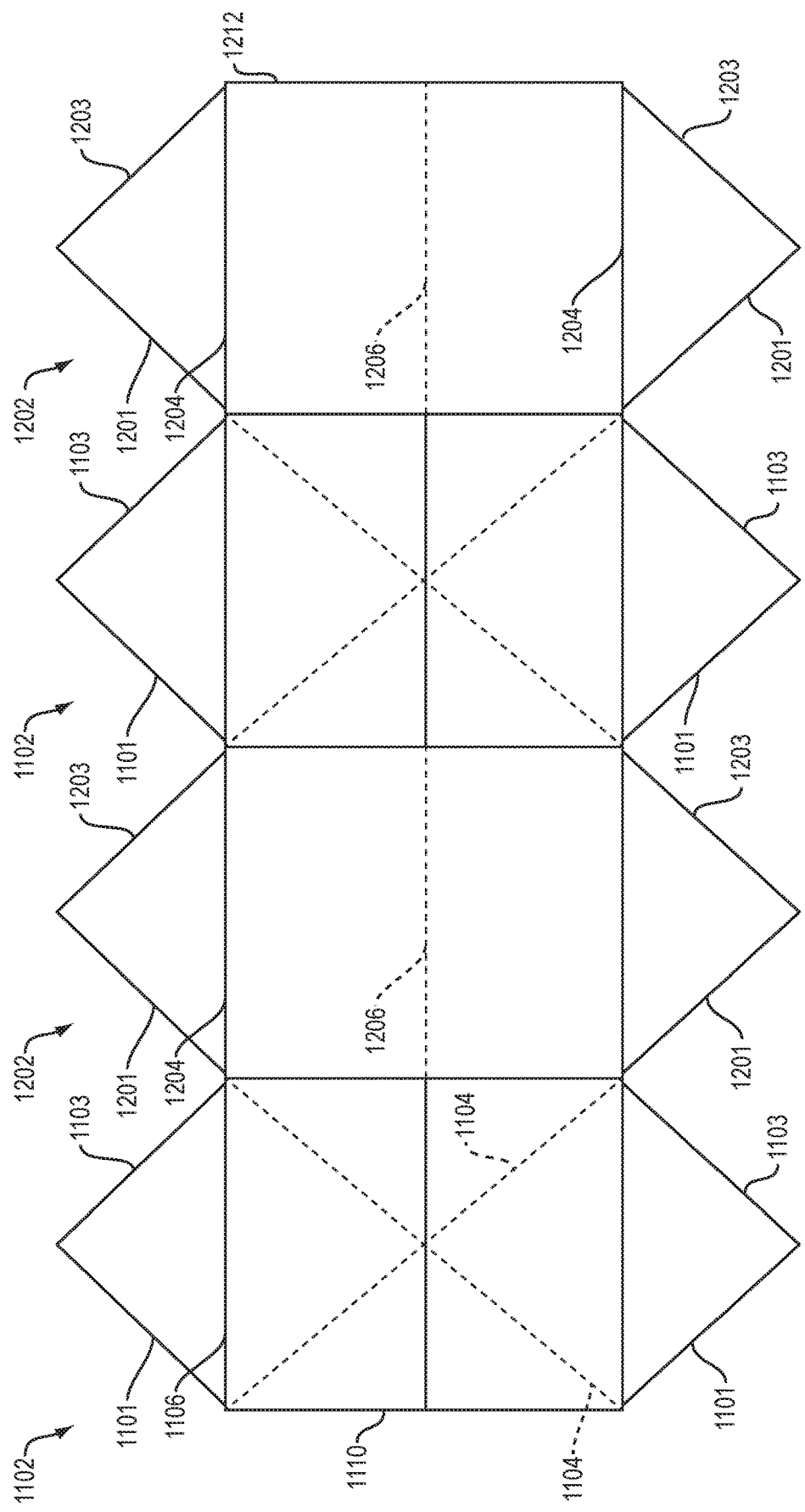
FIG. 13 depicts an exploded view of alternating patterned pieces of films to form a biocontainer, according to embodiments of the disclosure.

FIG. 13 depicts an exploded view of alternating patterned pieces of films 1102 and 1202, according to embodiments of the disclosure. As above, various pieces of the films 1102 and 1202 may be joined together to form articulating biocontainers. For example, the film 1102 has edges 1101 and 1103, which can be joined to the edges 1201 and 1203 of film 1202. As above, the joining can be accomplished by heat-staking, with heat and or pressure, sealing, bonding, welding and other methods for joining plastic films as is known to those in the art. Also, the first side 1110 of the film 1102 can be joined with the second side 1212 of the film 1202 to produce a modified balloon fold tote or biocontainer. Ports (not shown) can be added to the tote or biocontainer for inflation or for delivering/removing biological fluids, powders, and/or processing aids. In addition, the ports may be configured to house sensors capable of monitoring process variables of (e.g., temperature, pH, conductivity, oxygen levels, carbon dioxide levels, foam heigh, etc.) the contents of the tote or biocontainer. Furthermore, one or more openings (e.g. elongated openings) (also not shown) can be added to the tote or biocontainer that is configured to function as a viewing window. When in the expanded state, the tote or biocontainer can have a vacuum assist or have pressure applied to depress into a state for shipping or storage.

Figure 14:
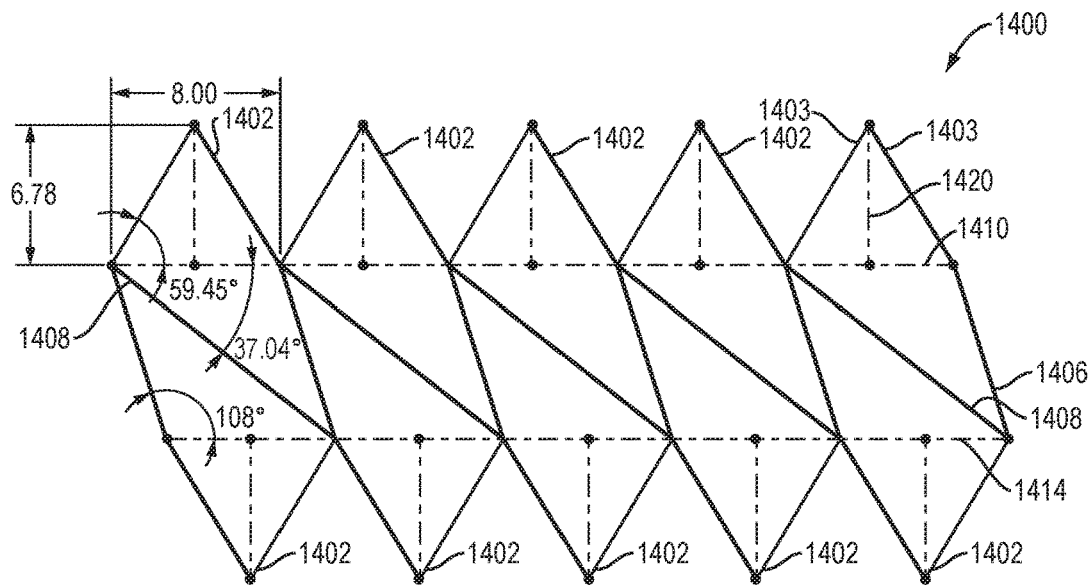
FIG. 14 depicts a plurality of films adhered together for forming a spiral fold, according to embodiments of the disclosure.

FIG. 14 depicts a plurality of films 1402 adhered together for forming a spiral fold 1400, according to embodiments of the disclosure. As shown, ten films 1402 are joined at articulation joints 1408. In practice, as many films 1402 as are desired can be joined. All dimensions shown are in inches. 1410 and 1414 are mountain articulated paths which were formed by creating a bow type articulation path with heat and pressure. 1408 articulation joints were formed by heat sealing. 1406 and 1402 are mountain articulations formed by heat sealing. 1420 is a reference line—no articulation need take place at this designation.

Figure 15:
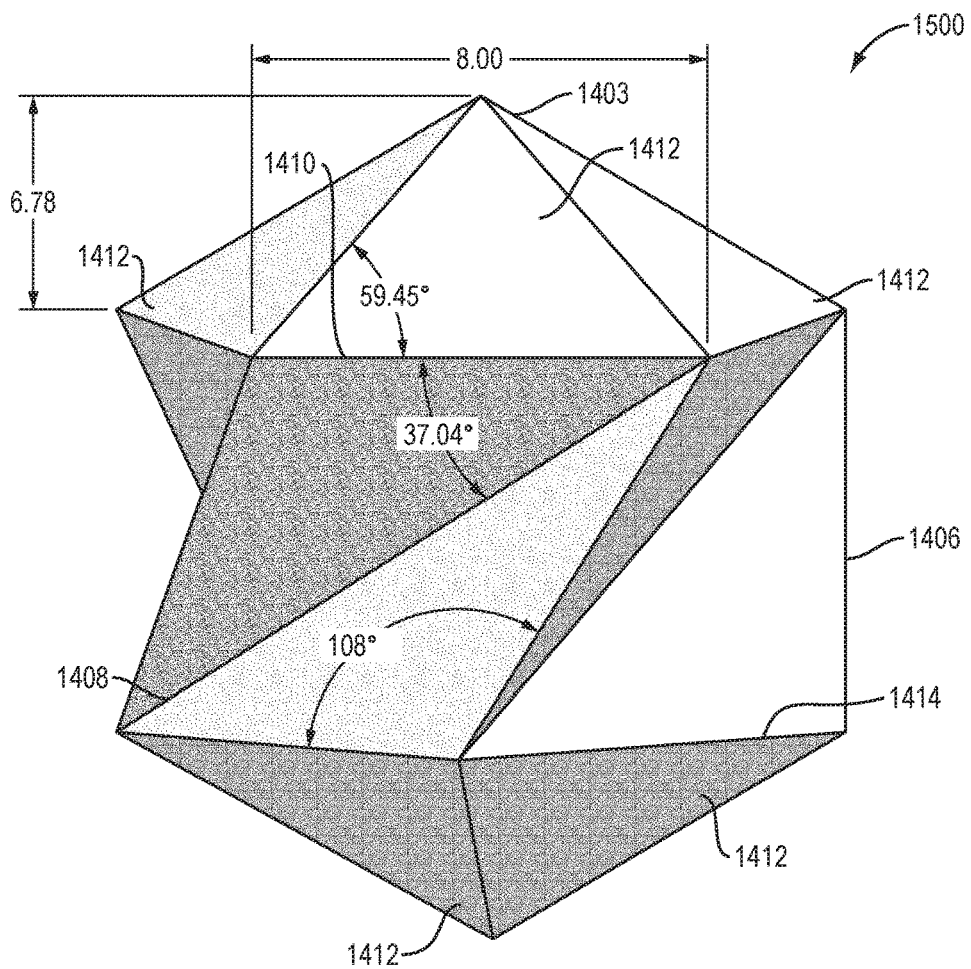
FIG. 15 depicts a spiral fold having a top film and a bottom film joined therewith, according to embodiments of the disclosure.

FIG. 15 depicts a regular spiral fold having a top film and a bottom film joined therewith, according to embodiments of the disclosure.

Figure 16A:
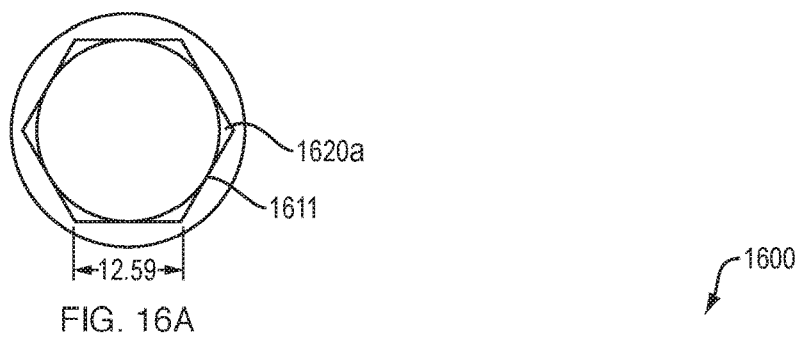
FIGS. 16A-16B depict a mirrored double spiral, according to embodiments of the disclosure.
Figure 16B:
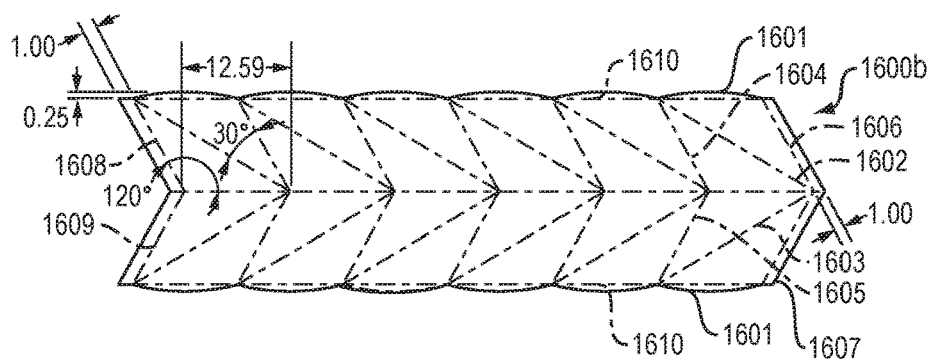

FIGS. 16A-16B depict a mirrored double spiral, according to embodiments of the disclosure. FIG. 16A depicts a mirrored double spiral, according to embodiments of the disclosure. 1620a, 1620b represent the top and bottom panels of a hexagonally designed biocontainer. The top and bottom panels 1620a (as in FIG. 16A), 1620b (as in FIG. 16B) are heat sealed to the articulated panel 1600b utilizing the tabs 1601 on film body 1600b. 1600b is patterned with a hexagonal reverse double spiral pattern. 1602 and 1603 are valley articulated paths formed with heat and pressure. 1604 and 1605 are mountain articulated paths formed with heat and pressure. 1606 and 1607 join side 1608 and side 1609 in a heat mountain articulation. Reference lines 1610, 1611 from the biocontainer body from the biocontainer top and bottom align using tabs 1601 to facilitate hear sealing in the mountain direction. Together with a top 1620a and a bottom (not shown) and one or more ports and other fittings, the design is capable of folding flat and expanding into a biocontainer, as shown below. The top 1620a may comprise any suitable film for biocontainers.

Figure 17:
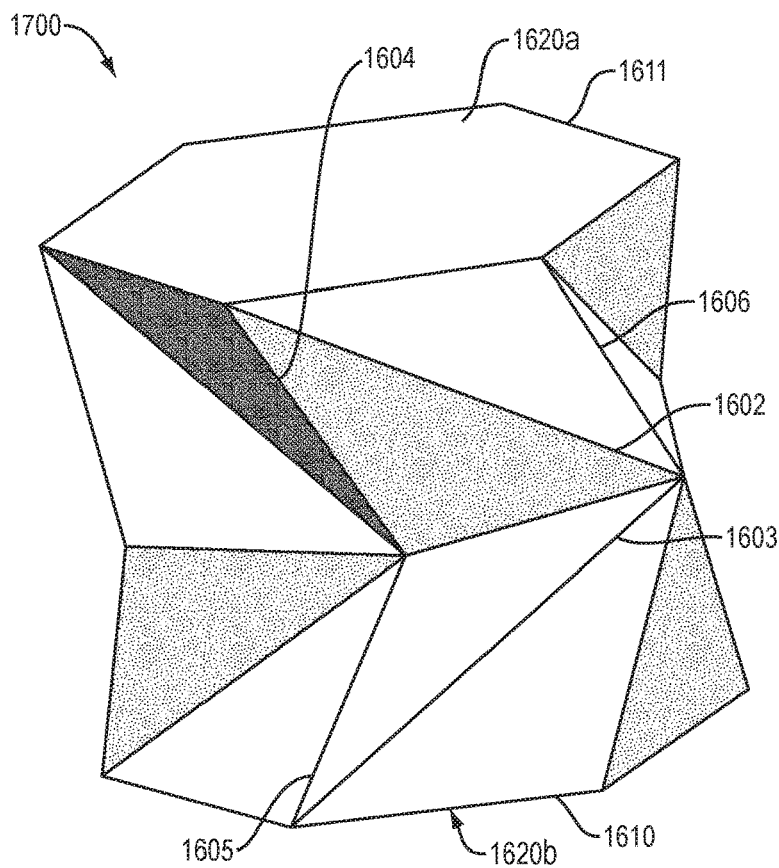
FIG. 17 depicts a mirrored double spiral with a top and a bottom assembled to form a biocontainer in an expanded state, according to embodiments of the disclosure.

FIG. 17 depicts a mirrored double spiral design assembled with a top 1620a and a bottom 1620b to form a biocontainer 1700 in an expanded state, according to embodiments of the disclosure. The biocontainer 1700, in its expanded state, has an inner volume for processing or storing fluids, such as biofluids. The biocontainer 1700, having articulations 1602, 1603, 1604, 1605, can expand and fold flat along the articulations 1602, 1603, 1604, 1605 repeatably, wherein crinkling of the film 1600b along non-articulated paths is lessened or eliminated. Accordingly, the biocontainer 1700 can be expanded and flattened a plurality of times, e.g., during manufacture, integrity testing, initial expansion for use in bioprocessing, re-folding, expanding and re-integrity testing, subsequent use, and the like without becoming damaged.

In embodiments according to the disclosure, any of the biocontainers described herein, which comprise any of the films and/or paths/pathways, are a single formed of a single layer of a plastic film or of a single calendared film or a multi-layer plastic laminate. Also, any of the embodiments of the biocontainers described herein may further comprise a removable contact layer film so that the outer biocontainer can be re-used. The removable contact layer film may be disposed on an internal portion of the inner volume of the biocontainer so that it contacts a biological fluid. In some embodiments, a plurality of removable contact layer films are disposed on a single biocontainer, wherein one of the plurality of removable contact layer films are removed with each use or processing of a biological fluid. In some embodiments, the removable contact layer film also comprises articulations. In some embodiments, the removable contact layer film comprising the articulations is attached to the biocontainer. In some embodiments, the removable contact layer film comprising the articulations is not adhered to the biocontainer.

Figure 18A:
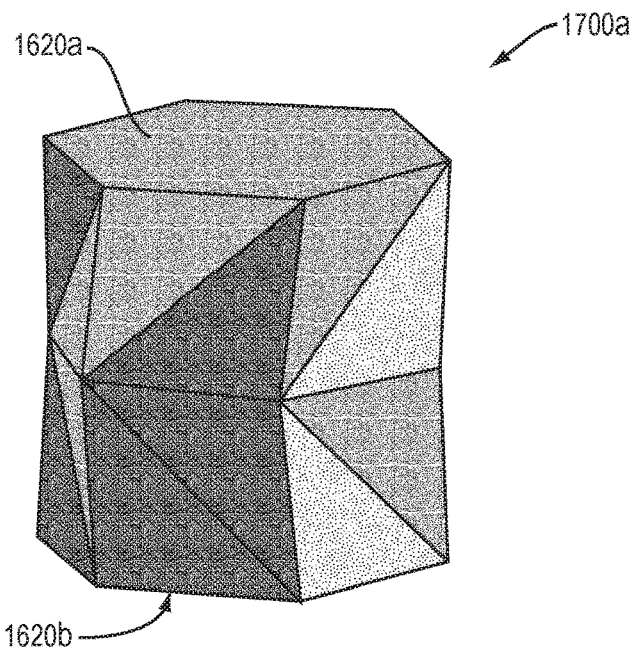
FIGS. 18A-C depict the mirrored double spiral design assembled with a top and a bottom to form a biocontainer, as in FIG. 17, in a fully expanded state, according to embodiments of the disclosure.
Figure 18B:
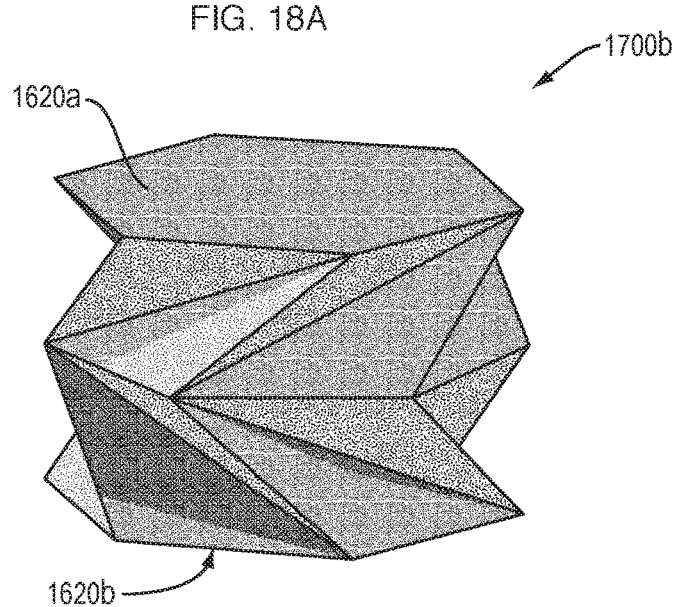
Figure 18C:
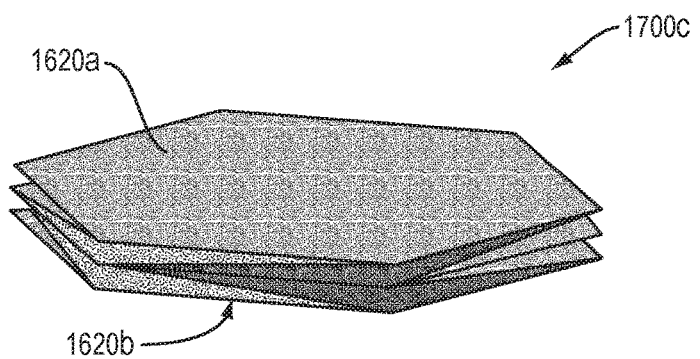

FIGS. 18A-C depict the mirrored double spiral design assembled with a top and a bottom to form a biocontainer, as in FIG. 17, in a fully expanded state, according to embodiments of the disclosure. FIG. 18A depicts the mirrored double spiral design assembled with a top 1620a and a bottom 1620b to form a biocontainer 1700, as in FIG. 17, in a fully expanded state, according to embodiments of the disclosure. 1700a depicts the biocontainer 1700 in a fully expanded state, 1700b depicts the biocontainer 1700 in a partially compacted state, and 1700c depicts the biocontainer 1700 in a fully compacted state. By way of example, and not limitation, 1700a may comprise a height of approximately 60-65 cm, 1700b might have a height of approximately 35-40 cm, as in FIG. 18B, and 1700c, as in FIG. 18C, might have a height of approximately 4-6 cm. Using these measurements, the biocontainer 1700 would be suitable for a 100 L application.

Figure 19A:
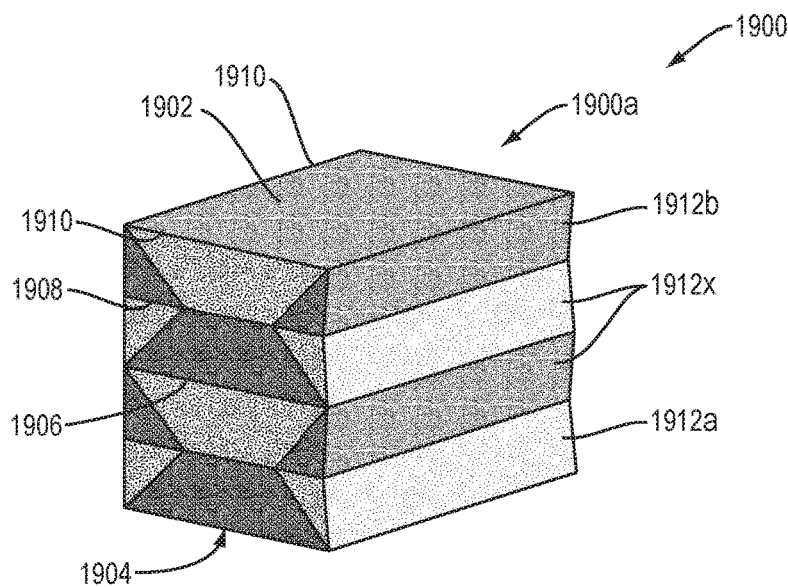
FIGS. 19A-C depict a tessellated square biocontainer, according to some embodiments of the disclosure.
Figure 19B:
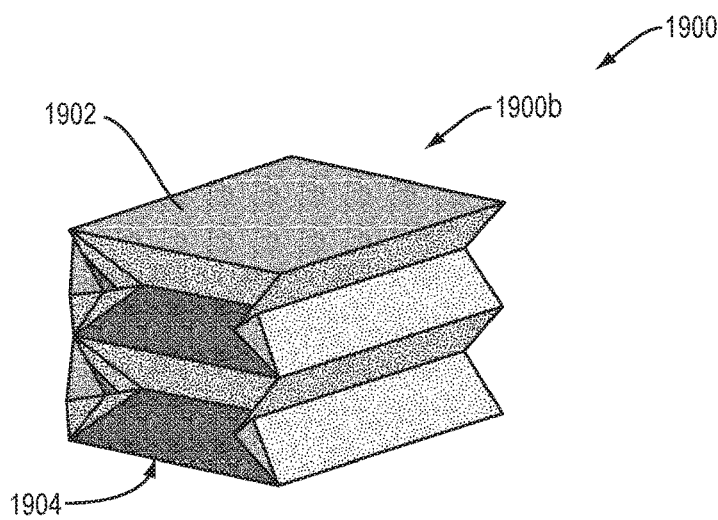
Figure 19C:
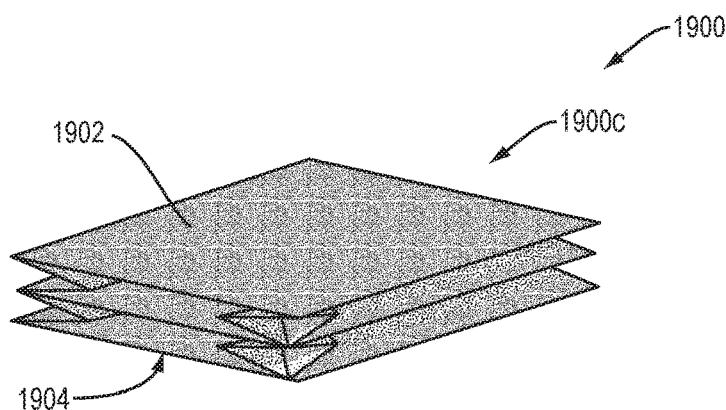

FIGS. 19A-C depict a tessellated square biocontainer, according to some embodiments of the disclosure. FIG. 19A depicts a tessellated square biocontainer 1900, according to some embodiments of the disclosure. The biocontainer 1900 comprises tessellations 1906 and 1908 similarly as those described above. The biocontainer 1900 is, in some embodiments, rectangular and, in some embodiments, square. As shown, the biocontainer 1900 has a top surface 1902 and a bottom surface 1904 comprising approximately 30-32 cm sides 1910, as shown in FIG. 19A. The biocontainer 1900, as shown, depicts a four-plane tessellated biocontainer. The biocontainer 1900 has a top plane 1912b and a bottom plane 1912a, and a plurality of median planes 1912x. As shown, there are 2 planes between the top plane 1912b and the bottom plane 1912a. In practice, four median planes 1912x, six median planes 1912x, eight median planes 1912x . . . n median planes, etc., are within the scope of the disclosure. 1900a depicts the biocontainer 1900 in a fully expanded state, 1900b depicts the biocontainer 1900 in a partially compacted state, and 1900c depicts the biocontainer 1900 in a fully compacted state. By way of example, and not limitation, as in FIG. 19A, 1900a may comprise a height of approximately 58-60 cm, 1900b might have a height of approximately 30-32 cm, as in FIG. 19B, and 1900c might have a height of approximately 4-6 cm, as in FIG. 19C. Using these measurements, the biocontainer 1900 would be suitable for a 200 L application. A four plane biocontainer 1900 would have forty folds, a six plane biocontainer 1900 would have 60 folds.

Figure 20A:
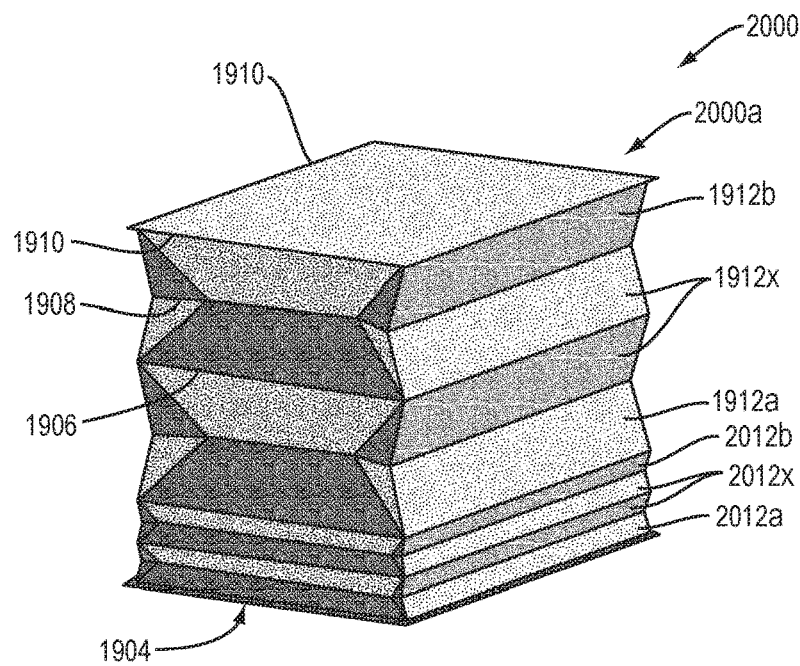
FIGS. 20A-C depict a second tessellated square biocontainer, according to some embodiments of the disclosure.
Figure 20B:
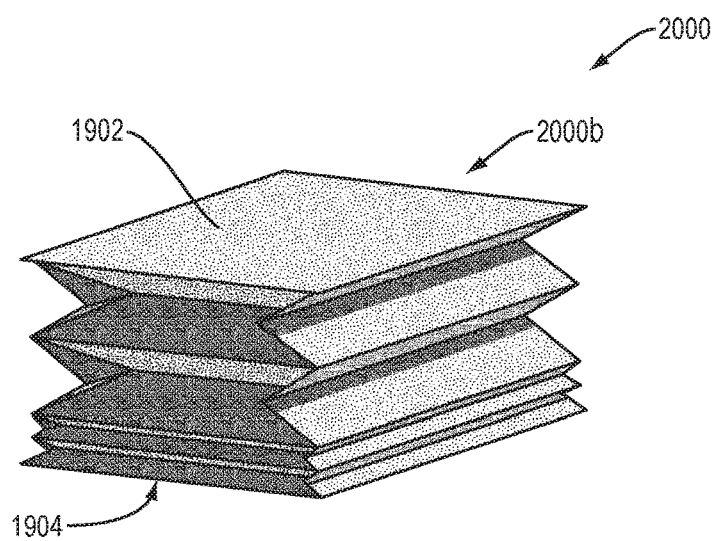
Figure 20C:
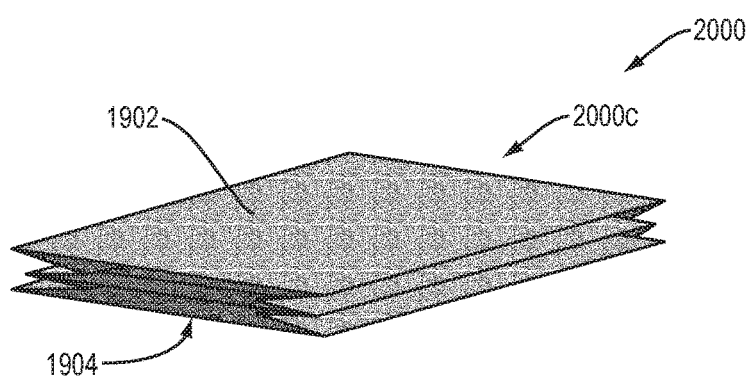

FIGS. 20A-C depict a second tessellated square biocontainer, according to some embodiments of the disclosure. FIG. 20A depicts a tessellated square biocontainer 2000, according to some embodiments of the disclosure. The biocontainer 2000a comprises tessellations 1906 and 1908 similarly as those described above. The biocontainer 2000a is, in some embodiments, rectangular and, in some embodiments, square. As shown, similar to the biocontainer 1900, the biocontainer 2000a has a top surface 1902 and a bottom surface 1904 comprising approximately 30-32 cm sides 1910, as in FIG. 20A. The biocontainer 2000, as shown, depicts a eight-plane tessellated biocontainer. The biocontainer 2000 has a top plane 1912b and a bottom plane 1912a, and a plurality of median planes 1912x. As shown, there are 2 planes between the top plane 1912b and the bottom plane 1912a. In practice, four median planes 1912x, six median planes 1912x, eight median planes 1912x . . . n median planes, etc., are within the scope of the disclosure. Furthermore, the biocontainer 2000 comprises unequal planes. As shown, the biocontainer 2000a has a plane 2012b (adjacent to the bottom plane 1912a) and a distal plane 2012a, and a plurality of median planes 2012x disposed between the plane 2012b and the distal plane 2012a. As shown, there are 2 planes between the plane 2012b and the distal plane 2012a. In practice, four median planes 2012x, six median planes 2012x, eight median planes 2012x . . . n median planes, etc., are within the scope of the disclosure. The biocontainer 2000 comprises similar expanded, partially compacted and fully compacted dimensions as the biocontainer 1900. An eight unequal plane biocontainer, as shown, has 80 folds. In this context, equal indicates that the plane have a similar height and unequal indicates a mixture of planes having similar heights and dissimilar heights, as if FIG. 20B and FIG. 20C.

Some embodiments according to the disclosure include a biocontainer, comprising a first film, the film having an interior and exterior side; and a second film, releasably adhered to the inner volume of the first film to form an outer biocontainer having a removable contact layer film.

Some embodiments of the disclosure include a biocontainer having a first film, the film having an interior and exterior side, forming an inner volume, and a second film, releasably adhered to the inner volume of the first film to form an outer biocontainer having a removable contact layer film, wherein the removable contact film layer permits the outer biocontainer to be re-used for separate bioprocessing processes. In some embodiments, the second film comprises articulations. In some embodiments, the biocontainer includes one or more articulating elements are disposed on or within the first film, the articulating elements comprising at least one of a folded hinge, a sealed joint, a thinned pathway, a bowed path, an embedded polymeric or metallic cylindrical fiber or rod, wherein the first film forms an inner volume. And, in some embodiments, the biocontainer further comprises a plurality of peelable contact film layers. In some embodiments, the peelable contact film layers comprise articulations.

Some embodiments of the disclosure comprise a biocontainer system that includes a first outer container and a first inner bag disposed within the first outer container. In some embodiments, the biocontainer system comprises a first inner bag that comprises articulations and is compacted within the first outer container. In some embodiments, the first inner bag is capable of being compacted, disposed within and removed from the first outer container. Also, in some embodiments, the first outer container is a flexible container comprising polymeric films. And, in some embodiments, the polymeric films of the first outer container comprise articulations.

It is to be understood that various manufacturing methods can be used to make the various films and biocontainers described herein. For example, a film may be folded into a bowed joint structure, as described above. The fold(s) can be disposed permanently into any of the films described herein using heat and pressure. In some embodiments, a sealed joint is formed by adhering two pieces of film together into a unitary piece. For example, two sheets of film, any of the films described herein, can be joined using one or a combination of heat, pressure and or vacuum assist and using a calendaring process, creating a joint that articulates in a single direction. Any of the articulations described herein can be created by biasing films in desired directions. In some embodiments, articulations are created by etchings and/or scoring of the film. In some embodiments, articulations are created using ablations of the film. In some embodiments, articulations are produced via the use of roller heaters having a pattern on the roller. In some embodiments, articulations are created by adhering or embedding a rod-like structure into the film. The rod-like structure may comprise, for e.g., a rigid or flexible, solid or hollow, cylindrical or semi-cylindrical members that are comprised of metals and/or polymers. In some embodiments, a pathway formed between two pieces of films or panels comprises air or another fluid to stiffen and/or create articulations within a film.

In some embodiments, articulations are formed within films by forming folds or rigid channels, weaker channels, and/or joints using vacuum forming, embossing, folding and pressing, 3D printing, and/or ablating processes. For example, a panel of film can be cut, such as flash cut or die cut. A Gantry system, housing a 3D printer, could print an inductive or a conductive gasket onto the panel. Tabs could be attached to the panel, wherein the panel can be pulled over a bar, wherein the panel would be wrapped or clamped and heated (such as by heating with a laser or an induction heater) to form articulated channels for tessellation. A top bar and a bottom bar can be used to produce a mountain fold(s) and a valley style fold(s). In other words, a bar having a suitable cross-sectional shape, i.e., symmetrical shapes, oval, circular, etc., or non-symmetrical shapes can be placed on a film, wherein the film is folded over itself, the bar heated, and removed, creating a tessellation, wherein the film retains the tessellation.

Figure 21:
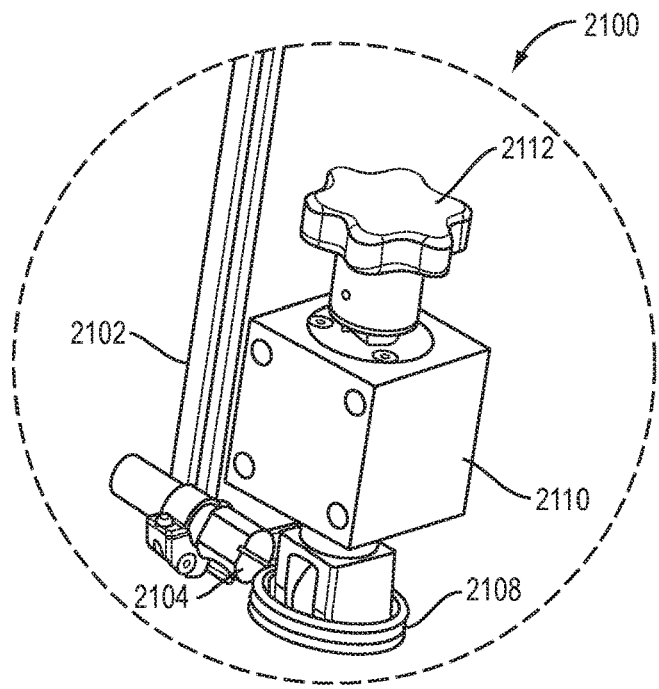
FIG. 21 depicts apparatus comprising an induction coil and a metallic wheel, according to embodiment of the disclosure.
Figure 22:
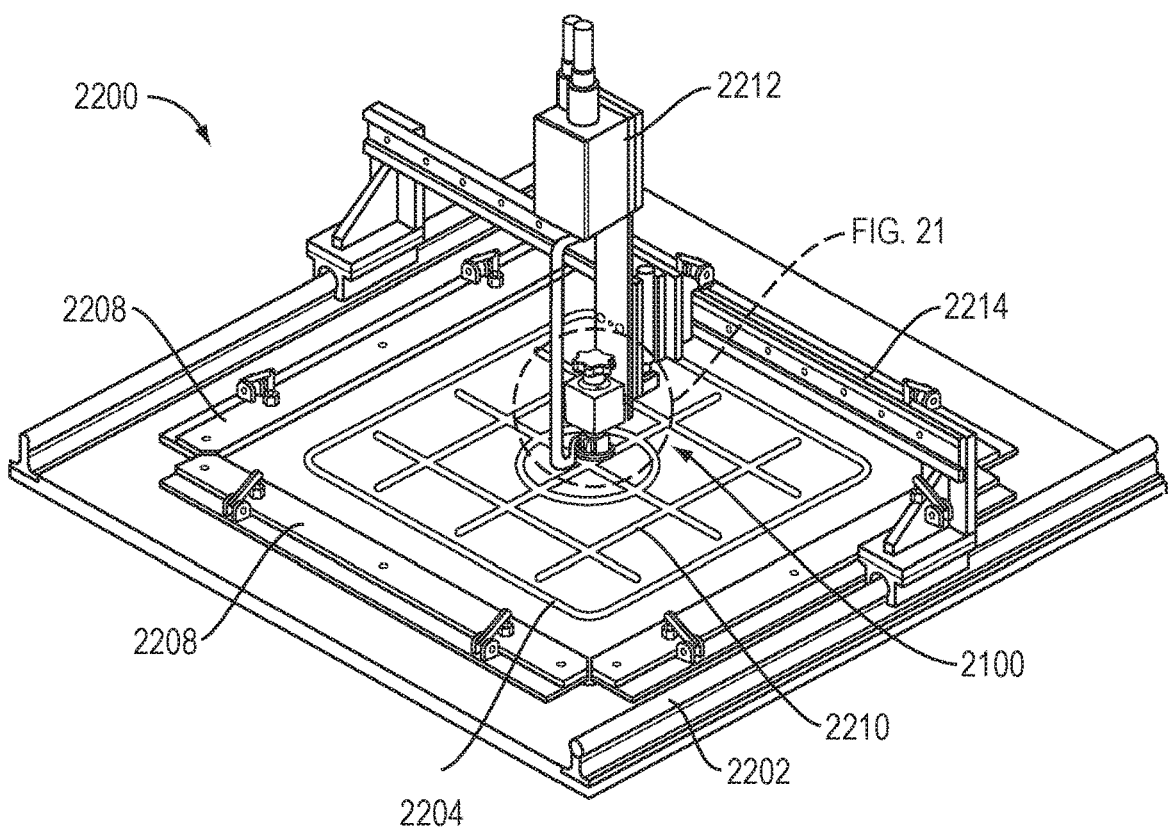
FIG. 22 depicts the apparatus of FIG. 21 disposed on a gantry positioning system, according to embodiments of the disclosure.

FIGS. 21 and 22 depicts a system for tessellating films, according to embodiments of the disclosure. FIG. 21 depicts apparatus 2100 comprising an induction coil 2102 and a metallic wheel 2108. Power supplied to the induction coil 2102 becomes heated, which in turn heats the metallic wheel 2108. In some embodiments, the metallic wheel 2018 comprises a stainless steel. The apparatus 2100 may further comprise a temperature sensor and controller 2104. For example, the temperature sensor and controller 2104 may be an infrared controller. A housing 2110 houses a transmission for controlling rotation of the metallic wheel 2108. A knob 2112 is connected with the metallic wheel 2108, directly or indirectly, allowing an operator to rotate the metallic wheel 2108. FIG. 22 depicts the apparatus 2100 disposed on a gantry positioning system 2200. The gantry positioning system 2200 permits the apparatus 2100 to move in three axes—x, y, and z. The apparatus 2100 is disposed on a boom 2212 for moving the apparatus in a z direction. The apparatus 2100 is also disposed on a support 2214, which rides on rails 2202 for moving the apparatus in x, and y directions. In operation, the system for tessellating films works by placing a film to be tessellated on a tooling plate 2204. In some embodiments, the tooling plate 2204 comprises recesses and/or ridges 2210. Moving the apparatus 2100 in a desired pattern while heated allows an operator to dispose tessellations into a film. Optionally, the film is held down by one or more clamps 2208. The tooling plate 2204 can be made of any suitable material, for example, steel, aluminum, ceramics, silicone rubbers, etc.

Figure 23A:
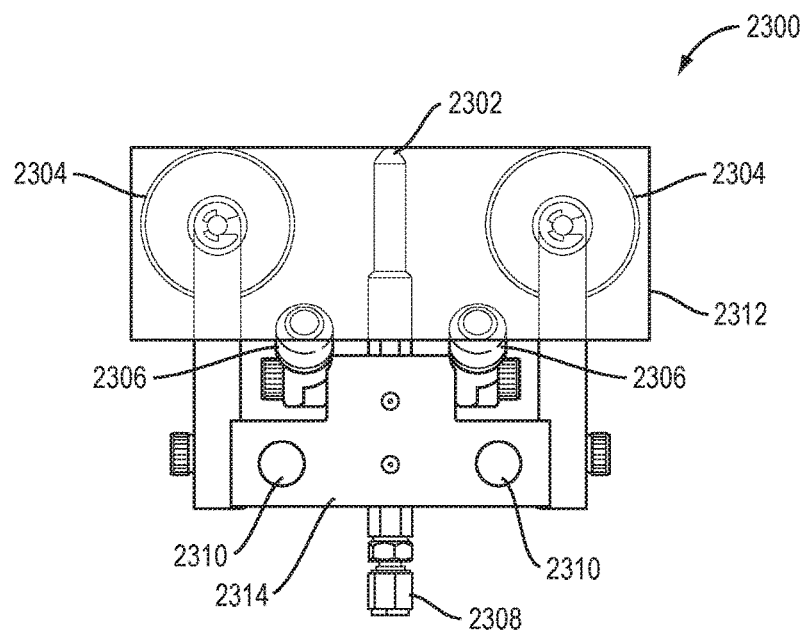
FIGS. 23A-B depict a film forming tool for forming a tessellated film, according to embodiments of the disclosure.
Figure 23B:
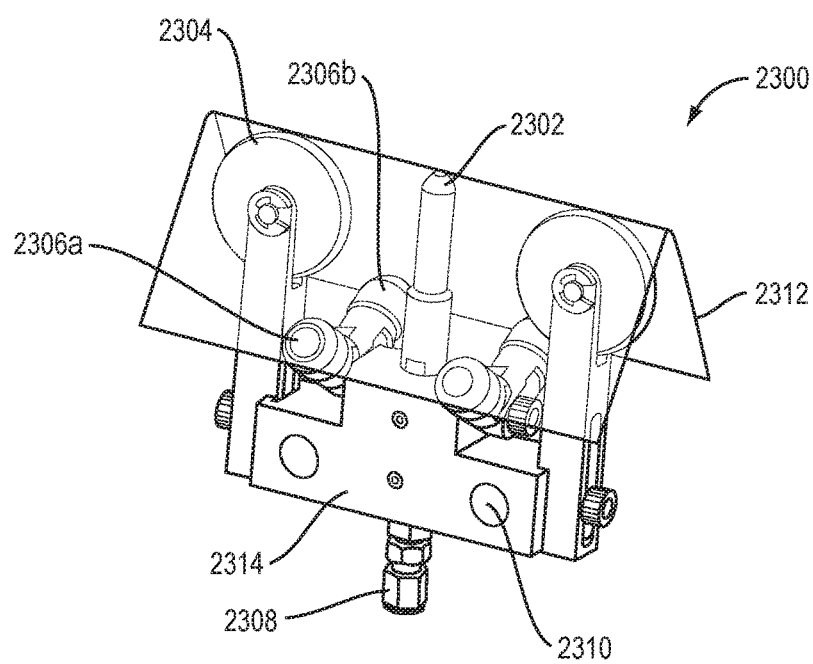

FIGS. 23A-B depict a film forming tool for forming a tessellated film, according to embodiments of the disclosure. FIG. 23A depicts a film forming tool 2300 for forming a tessellated film 2312, according to embodiments of the disclosure. FIG. 23A depicts a front view of the film forming tool 2300 for forming a tessellated film 2312. The film forming tool 2300 comprises an induction heating tip 2302 disposed between two rotary wheels 2304, which are opposite each other and can be made of any suitable material, e.g., plastic, ceramic and/or metal. The rotary wheels 2304 support the film 2312. The induction heating tip 2302 projects from a tip housing 2314. The induction heating tip 2302 may, optionally, have a channel extending into it and in fluid communication with a fitting 2308 for providing air, such as hot air, to the tip 2302. The tip housing 2314 may also include conduits 2310, which may have a loop or tube attached thereto (not shown) for creating a cooling conduit. The tip housing 2314 may also have roller ball(s) 2306 attached, which are at any angle less than 90° from an axis through the induction heating tip 2302. The roller ball(s) 2306 are, for example, a VLIER® pin or ball bearing that rolls freely so that drag marks are minimized on the film 2312. FIG. 23B depicts a perspective view of the film forming tool 2300 for forming a tessellated film 2312 depicted in FIG. 23A. In at least some embodiments, the angle that any single roller ball 2306 makes with the heating induction tip 2302 is 30°. Accordingly, if there is a second roller ball 2306b opposite a first roller ball 2306a, both of which are 30° from the induction heating tip 2302, the film disposed thereon would have a folded angle of 60°. In practice, the folded angle of the film 2312 can be 20-160° or even closely approximating 180°. The film forming tool 2300 for forming a tessellated film 2312 can be placed on any suitable fixture or frame. As stated above, the flexible films may comprise a laminate film structure with a lower melting point material internal to an external higher melting point polymer. Also, in some embodiments, the flexible films comprise a laminate film structure with a lower melting point material surrounding a higher melting point woven, knit, or non-woven material and, in some embodiments, heat setting the lower melting point material combined with controlling the degree of articulation (150° vs 180°) permits a tessellated vessel to deploy with less resistance.

Figure 24:
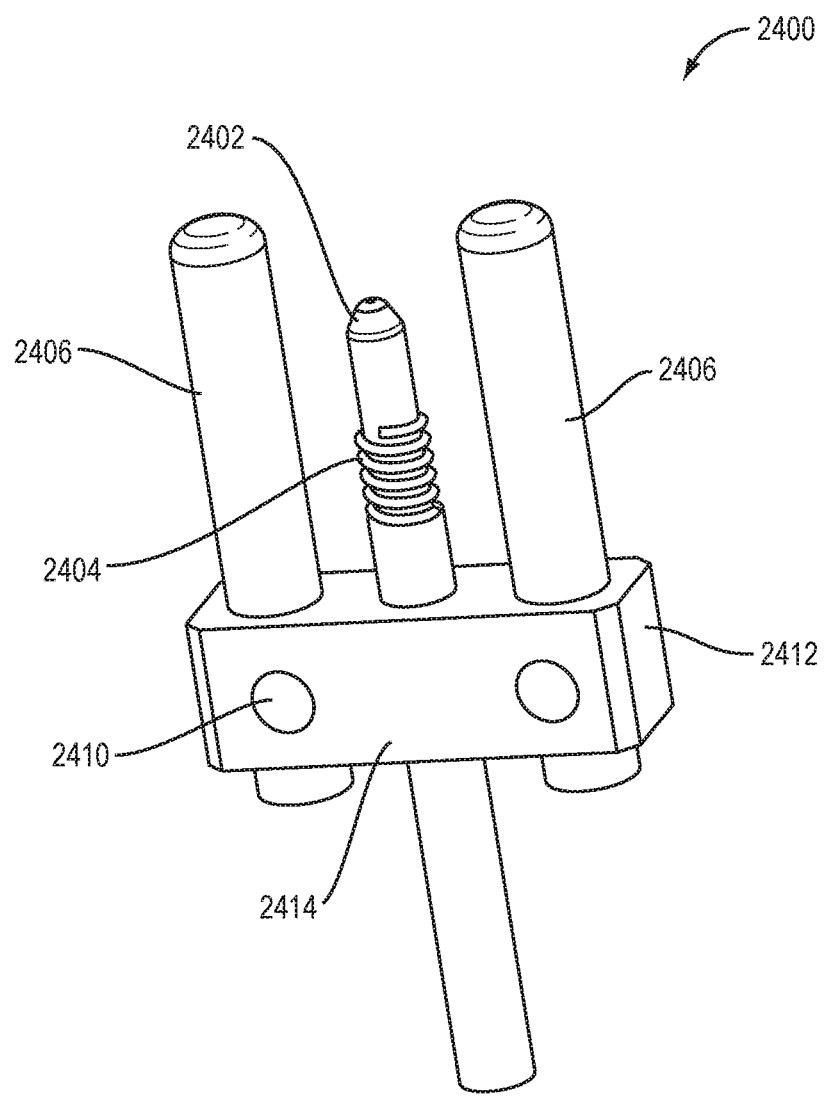
FIG. 24 depicts a system that comprises a retracting inductive heating tip for forming tessellated films, according to embodiments of the disclosure.

FIG. 24 depicts a system 2400 that comprises a retracting inductive heating tip 2402 for forming tessellated films, according to embodiments of the disclosure. The retracting inductive heating tip 2402 comprises two outrigger folding rods 2406 that are opposite each other, wherein the inductive heating tip 2402 and a coil 2404 are disposed therebetween and can become recessed or projecting from a plane across the two outrigger folding rods 2406. The retracting inductive heating tip 2402 comprising the two outrigger folding rods 2406 are disposed on a housing 2412. The housing 2412 may comprise channels 2410 for providing a cooling fluid therethrough. Also, the induction heating tip 2402 may comprise a hole (not shown) for air flow velocity control therethrough. The housing 2412 may optionally comprise a bushing 2412 for thermally insulating the inductive heating tip 2402 from the housing 2412.

FIGS. 25A-D depict a process for making, for example, the panels for making the biocontainer, a four-plane tessellated biocontainer, according to embodiments of the disclosure. FIGS. 25A-25D depict a process for making, for example, the panels for making the biocontainer 1900, a four-plane tessellated biocontainer, as shown in FIG. 19. FIG. 25A depicts a first retracting inductive heating tip 2402a in a system 2400 opposite a second a retracting inductive heating tip 2402b in a system 2400, wherein a film 2412 is disposed therebetween. In FIG. 25A, the inductive heating tip 2402a and 2402b are both in neither a recessed nor a projecting state. In FIG. 25B, the inductive heating tip 2402a projects outwardly in a y direction while the inductive heating tip 2402b becomes recessed in a y direction. In FIG. 25C, the inductive heating tip 2402a projects even further outwardly in a y direction, while the inductive heating tip 2042b becomes further recessed. The systems 2400 can then move in a positive and/or negative z direction to form a tessellated film having tessellation 1906, as described above. FIG. 25D depicts the systems 2400 in an angled configuration with respect to the horizontal to form a tessellation 1908. The systems 2400 can be disposed on a gantry system, as described above, on any table using a fixture, and/or with a computer-controlled robot to automatically program the movements of the systems 2400 and/or a table having the film 2412 disposed thereon.

Figure 26:
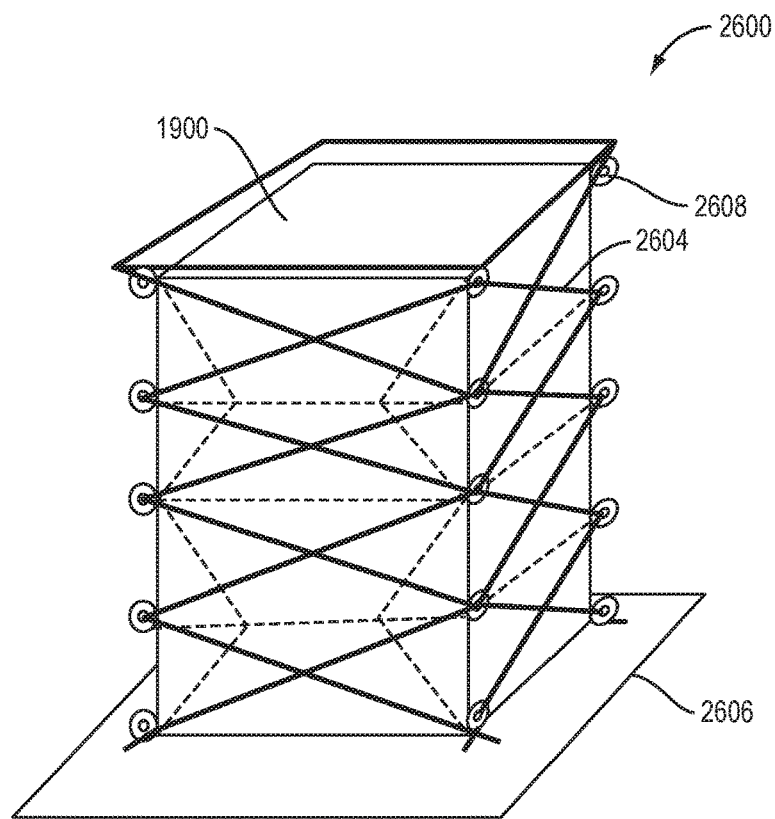
FIG. 26 depicts a biocontainer, for example, the biocontainer described in FIG. 19, further comprising tabs and a bag support system, according to embodiments of the disclosure.

FIG. 26 depicts a biocontainer, for example, the biocontainer 1900 described above, further comprising tabs 2608 and a bag support system. The biocontainer 1900 has a rectractable scaffolding 2604 disposed therein, and sits, optionally, on a platform 2606. As shown, the retractable scaffolding 2604 is a scissor style scaffolding. It is to be understood that the scissor style scaffolding 2604 could be added to any of embodiments described in this disclosure and other biocontainers.

Figure 27:
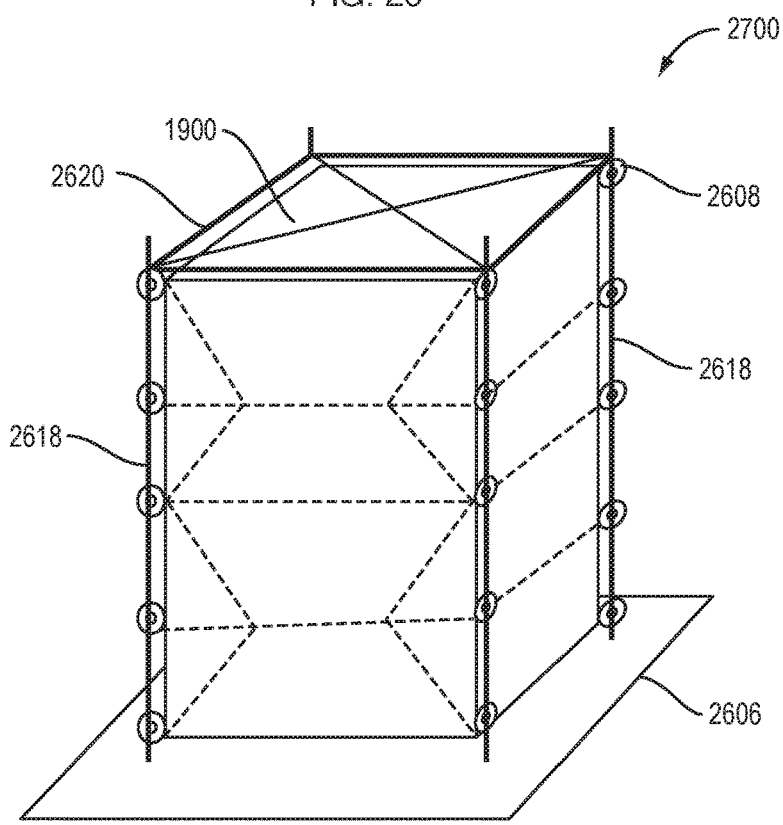
FIG. 27 depicts a biocontainer, for example, the biocontainer described in FIG. 19, further comprising tabs and a second bag support system.

FIG. 27 depicts a biocontainer, for example, the biocontainer 1900 described above, further comprising tabs 2608 and a second bag support system. The biocontainer 1900 has a series of support poles 2618 disposed within the tabs 2608, and sits, optionally, on a platform 2606. An upper support frame 2620, optionally, can be placed through the tabs 2608. As shown, the support poles 2608 support the perimeter of the biocontainer 1900. It is to be understood that the tabs 2608 could be added to any of embodiments described in this disclosure and other biocontainers.

It is to be further understood that any of the flexible films and/or biocontainers described herein may comprise a series of staggered tessellations. For example, a plane may comprise a first series of discontinuous tessellations while a neighboring plane comprises a second series of discontinuous tessellations that do not line up vertically with the first series of tessellations, i.e., staggered tessellations. In other words, although the tessellations do not comprise a cut through an entire film, the tessellations have a staggered visual design akin to those of Kirigami concepts. It is to be further understood that stronger articulations can be constructed, such as having additional channel supports by using a deeper articulation or by having a "W" or "M" type articulation channel. Also, the strength of a biocontainer can be a function of polymer selection as well as the types of articulations. For deployment, it is sometimes desirable for the articulations to "spring back" in some designs, which can be achieved using various tessellations, articulations, films, plastics and/or laminates and/or composites having stronger or weaker flexural modulus properties.

At least some of the films described herein are created using the principles of origami, i.e., structures manufactured using square, rectangular, parallelpiped shaped films. At least some of the films described herein are created using the principles of kirigami, i.e., structures manufactured using non-parallelpiped shaped films, i.e., triangular, rhomboidal, trapezoidal, truncated triangles, panels or pieces of film that are cut into desired shapes, etc., and/or the like. Biocontainers, bags, mixing bags bioreactors, and other containers are used interchangeably herein. Many known structures, such as paper bag folds, valley folds, mountain folds, and the like, are considered within the scope of embodiments of the disclosure.

EXAMPLES OF SOME FILM STRUCTURES

Film structures according to some embodiments of the invention can comprise any film suitable for biocontainers, bioreactors, cryobags, and/or the like as are known to those in the art. In some embodiments, the films described herein are single layer films. In some embodiments, the films described herein are multi-layer films. In some embodiments, the films described herein comprise gas-impermeable layers and/or fabric substrates. Any of the films described herein are capable of having articulations imparted therein, e.g., thinned paths, ablated paths, scored paths, bowed paths, In some embodiments, the films comprise laminated films as marketed under the PureFlex™ brand by MilliporeSigma Corp., of Burlington, MA, USA. The PureFlex™ film comprises a first ultralow density polyethylene layer, an EVOH layer disposed thereon, an EVA resin layer disposed on the EVOH layer, and a second ultralow density polyethylene layer disposed on the EVA resin layer, wherein the PureFlex™ film is approximately 0.25 mm in thickness. In some embodiments, the first ultralow density polyethylene layer is a fluid contact layer. In some embodiments, the second ultralow density polyethylene layer is a fluid contact layer. Also, in some embodiments, the EVA resin layer comprises an EVA copolymer resin. For example, the EVA copolymer resin may comprise approximately 20-30% by weight ethylene vinyl acetate. In some embodiments, the EVA resin layer comprises approximately 28% by weight ethylene vinyl acetate. In some embodiments, the EVA resin layer comprises approximately 28% by weight ethylene vinyl acetate blended with low density polyethylene. In some embodiments, the EVA resin layer comprises an ELVAX® resin as marketed by the E.I. duPont De Nemours of Wilmington, DE, USA. The Pureflex™ film, as described below, was a multilayered laminated film having an inner contact zone, an intermediate oxygen barrier zone and an outer protective zone formed of plastic only. The film was approximately 0.020 inches in thickness (0.50 mm). In some embodiments, the PureFlex® film has a contact layer that comprises an ethylene alpha-olefin resin. For example, some exemplary ethylene alpha-olefin resins are marketed under the brand AFFINITY® by Dow Corp., of Midland, MI, USA.

A sample of Pureflex™ film was modified so that the outer zone had a layer of EVOH resin, for e.g., as provided by Kuraray Co., Ltd, Premium Pack, GmbH, SOARNOL®, marketed by Soarus, LLC, Arlington Heights, IL, USA and/or others, to improve flex crack resistance. In some embodiments, the EVOH layer comprises an ethylene vinyl alcohol copolymer, optionally having a low melt flow rate. A sample of flat tube standard film with flex crack resistant resin was approximately 0.014-0.020 inches in thickness (0.35-0.50 mm).

A sample of the film according to the present disclosure was made by lamination of an inner contact zone formed of a polyolefinic resin, an intermediate zone containing a substrate, e.g., a nylon woven substrate, obtained from Sefar, Inc., of Buffalo, NY, USA, having a mesh count of 86 in both the weft and warp direction and a thickness of approximately 150 microns, oxygen barrier zone formed of an EVOH resin and an outer layer of a flex crack resistant resin with a tie layer between each zone.

The PureFlex™ film comprises a first ultralow density polyethylene layer, an EVOH layer disposed thereon, an EVA resin layer disposed on the EVOH resin layer, and a second ultralow density polyethylene layer disposed on the EVA resin layer, wherein the PureFlex™ film is approximately 0.25 mm in thickness. In some embodiments, the first ultralow density polyethylene layer is a fluid contact layer. In some embodiments, the second ultralow density polyethylene layer is a fluid contact layer. Also, in some embodiments, the EVA layer comprises an EVA copolymer resin. For example, the EVA copolymer resin may comprise approximately 20-30% by weight ethylene vinyl acetate. In some embodiments, the EVA resin layer comprises approximately 28% by weight ethylene vinyl acetate. In some embodiments, the EVA resin layer comprises approximately 28% by weight ethylene vinyl acetate blended with low density polyethylene. In some embodiments, the EVA resin layer comprises an ELVAX® resin as marketed by the E.I. duPont De Nemours of Wilmington, DE, USA.

Any of the embodiments of the films 100a, 100b, 100c, 100d, 200a, 200b, 200c, 200d . . . may be used individually or in any combination with each other. In some embodiments of the films 100a, 100b, 100c, 100d, 200a, 200b, 200c, 200d . . . comprise a multi-layer laminate. Any embodiments of the films 100a, 100b, 100c, 100d, 200a, 200b, 200c, 200d . . . comprise an inner contact zone. The inner contact zone comprises a first face, which is in contact with the liquid within an inner volume of a biocontainer (described herein) formed from the films. The inner contact zone may be formed of one or more layers of material that are inert to the liquids that may be in contact with the film and which is/are also low in extractables that might enter the liquid in contact with the inner contact zone or the first front face of the films. Such materials include, but are not limited to, various polyolefins such as polyethylene. Some embodiments include low density polyethylene, linear low density polyethylene, ultra low density polyethylene, medium density polyethylene, and the like. Outward of the inner contact zone is a gas impermeable zone formed of one or more layers of resins that are gas impermeable. Such resins include but are not limited to polymers, such as EVA and EVOH, and may also comprise various metal foils such as aluminum, aluminum alloys, and/or various combinations thereof. Outward of this gas impermeable zone is optionally an outer strength zone formed of one or more layers which provides support, burst resistance, and some measure of protection, e.g., abrasion-resistance, to the remaining zones of the films. Such resins include but are not limited to various grades of polyethylene such as high-density polyethylene, polypropylene, nylons, PET, EVA, polyamide and the like.

Each of the inner contact zone, gas impermeable zone, and outer strength zone are represented by one layer following lamination and/or calendaring although each zone may be formed of one or more layers bound together, wherein the various zones are formed together as an integral film. For example, one or more of the zones, or each zone, can be formed of several layers, according to some embodiments of the disclosure. Also, similar polymer resins can be formed with tie resins between one or more of the zones and/or the layers that may make each of the inner contact, gas impermeable and outer strength zones. Tie layers may comprise, for e.g., polyurethanes, blends of EVA and polyethylenes, e.g., low density polyethylene, and other tie layers for forming laminates as is known to those in the art.

Any of some of the embodiments of the films described herein may further comprise a substrate. The substrate may comprise a woven material, a nonwoven material, a spunbonded material or, a netting material, such as DELNET® film, which is an aperture or porous stretched film, marketed by Hercules, Inc., of Wilmington, DE, USA. The substrate may comprise polymer fibers or yarns, metal fibers or yarns, glass fibers or yarns or carbon fiber or yarns or combinations thereof. Polymer substrates, generally, woven, nonwoven or netted can be formed of materials such as nylons, KEVLAR® and other amides, PET, EVA, polyethylenes, polypropylenes and the like.

Polymeric woven fabrics can be formed of any of the previously mentioned polymers. Polymeric woven fabrics are commercially available either as a fabric alone or a coated fabric which has a tie layer integrated within it. Such materials are available from a variety of companies such as Eastex Products Inc. of Holbrook, MA, USA; PGI Inc. of Charlotte, NC, USA; or Freudenberg & Co. of Manchester, NH, USA. Nonwovens can be for example spunbonded or blown materials and are commercially available for instance as TYPAR® or TYVEK® sheets from E.I. duPont De Nemours of Wilmington, DE, USA.

Any of the films described herein may comprise an inner contact zone further comprising one or more layers of material that are inert to the liquids that may be in contact with the film and/or which is/are low in extractables that might enter the liquid in contact with the inner contact zone. In some exemplary embodiments, the inner contact zone comprises, for example, a polyolefinic material, i.e., a polyethylene layer. In some embodiments, the polyethylene layer that is at least one of ultra-low density polyethylene (ULDPE), e.g., a density of 0.857-0.908 g/cm$^3$, a polyolefin plastomer, or a polyethylene-octene copolymer. In some embodiments, the polyethylene layer comprises ENGAGE® polyolefin elastomers, and some exemplary ethylene alpha-olefin and polyethylene-octene copolymer resins, as marketed by the Dow Corp. of Midland, MI, USA.

Any of the films described herein may comprise a gas impermeable zone formed of one or more layers of materials that are gas impermeable, such as EVA and EVOH, and may also comprise various metal foils such as aluminum, aluminum alloys, and/or various combinations thereof. In some embodiments, the gas impermeable zone comprises multiple layers, e.g., a polyethylene, such as an LDPE or LLDPE; a second polyethylene layer, such as ENGAGE® polyolefin elastomers, a tie layer, such as a modified polyethylene layer (for e.g., a LDPE modified with maleic anhydride), an EVOH layer, a second tie layer, a second polyethylene layer, and an EVA layer.

Any of the films described herein may comprise a substrate disposed between the inner contact zone and the gas impermeable zone. The substrate may provide burst resistance as well as strength for support during articulation and/or use. In some embodiments, the tie layer is embedded into the substrate. Preferred tie layers 14 include plastics such as poly (ethylene vinyl acetate) alone or blended with a different polymer such as polyethylene. In some embodiments, the tie layer comprises a blend of EVA and a low density polyethylene, wherein the EVA is a high flow EVA. For example, in some embodiments, the melt flow for the tie layer 14 may range from approximately 3-25 g/10 min. The tie layer may also be a polyurethane material.

A biocontainer having an inner volume defined by its sealed sides, top and bottom may be formed from any of the films described herein. The inner volume of the biocontainer can range from 10 milliliter to 3500 liters or greater. Typically, a variety of sizes, such as 1, 5, 10, 20, 50, 100, 200, 500, 1000 and 2000 liters although custom volumes therebetween, or even larger than 2000 L, may be constructed as desired or as appropriate for any particular bioprocessing operation. The biocontainer can used to store or process fluids, (gases, liquids or combinations of both) and/or solids and may be formed into a biocontainer or mixer or storage bag. For example, the biocontainer may be a mixer and may be used to mix various liquids together or a liquid or liquids with one or more solids such as buffer media, cell culture media and the like. It may also be a biocontainer or fermentor used to grow animal cells such as insect cells or mammalian cells, including Chinese Hamster Ovary cells (CHO); bacteria such as *E. coli*; yeasts; fungi; and the like. The biocontainer or bioreactor may be used for the storage or transport of liquids such as intermediate or finished pharmaceutical products. Various additions such as impellers, sensors, gas and liquid tube sets and the like, as are known to those in the art, may also be added as desired.

All ranges for formulations recited herein include ranges therebetween and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4, or 3.1 or more.

Reference throughout this specification to "one embodiment," "certain embodiments," "one or more embodiments," "some embodiments," or "an embodiment" indicates that a feature, structure, material, or characteristic described in connection with the embodiment is included in at least one embodiment of the disclosure. Therefore, the appearances of the phrases such as "in one or more embodiments," "in certain embodiments," "in one embodiment," "some embodiments," or "in an embodiment" throughout this specification are not necessarily referring to the same embodiment. Nonetheless, it is to be understood that any feature described herein can be incorporated within any embodiment(s) disclosed herein.

Publications of patent applications and patents and other non-patent references, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed:

1. A biocontainer, comprising:
a first film, the first film having an interior and exterior side;
articulating elements disposed on or within the first film, the articulating elements comprising a bowed path where a thickness of the first film remains unchanged across the bowed path or increase in proximity of the bowed path; and
a second film, optionally comprising articulating elements, joined to the first film to form the biocontainer having at least two walls and an inner volume defined by the at least two walls;
wherein the articulating elements permit the biocontainer to expand and collapse along the articulating elements,
wherein the first film is formed of one or more layers forming an inner contact zone, one or more layers of a gas impermeable zone, and one or more layers of polymers on an exterior side of the gas impermeable zone forming an outer strength zone,
wherein a substrate is incorporated into the first film between the inner contact zone and the gas impermeable zone, and the substrate is formed of a fibrous material, and
wherein the articulating elements are a double-jointed articulation that produces joints having flexibility in two directions, wherein combining the double-jointed articulation with patterns allow for folding in one direction and locking upon deployment in an opposite direction.

2. The biocontainer of claim 1, wherein the substrate is formed of a material selected from the group consisting of woven and non-woven fibrous material.

3. The biocontainer of claim 2, wherein the substrate has one or more openings formed in it to provide a device selected from the group of a viewing window, one or more ports for adding liquids, powders, processing aids, one or more ports for monitoring temperature, pH, conductivity, oxygen levels, carbon dioxide levels, foam height and other process variables, one or more ports for removing biological fluids, and/or one or more ports for housing sensors.

4. The biocontainer of claim 2, wherein the substrate has one or more elongate openings formed in it to provide a viewing window into an interior of the biocontainer.

5. The biocontainer of claim 2, wherein the substrate is formed of a material selected from the group consisting of polymers, metal fibers, carbon fibers and glass fibers.

6. The biocontainer of claim 1, wherein the substrate is formed of a material selected from the group consisting of the fibrous material in a form selected from the group consisting of woven and non-woven materials and the fibrous material is made of a material selected from the group consisting of nylon, polyester, aramids, carbon, metal and polyolefins.

7. The biocontainer of claim 1, wherein the second film is formed of a multilayered film.

8. The biocontainer of claim 1, further comprising zones of articulation and zones of non-articulation to create articulated joints.

9. The biocontainer of claim 1, wherein the biocontainer has a strength and/or rigidity capable of being a standalone biocontainer.

10. The biocontainer of claim 1, wherein the biocontainer can maintain an expanded state without being supported by a secondary container or of a separate supporting structure, permitting a system having reduced footprint compared with supported systems.

11. The biocontainer of claim 1, wherein the biocontainer has significantly greater flexural endurance, can be folded or compacted, expanded, folded or compacted, and expanded multiple times without failure.

12. The biocontainer of claim 1, wherein the biocontainer comprises a 2-dimensional (2D) or a 3-dimensional (3D) biocontainer capable of storing biological fluids.

13. The biocontainer of claim 1, wherein the biocontainer comprises a plurality of panels of film adhered to form a unitary structure.

14. The biocontainer of claim 1, wherein a rigidity of the biocontainer is further enhanced by constructing stiffer non-articulated zones.

15. The biocontainer of claim 1, wherein the articulating elements are created by thickening a cross section of the first film.

* * * * *